United States Patent
Totsuka

(10) Patent No.: US 11,343,428 B2
(45) Date of Patent: May 24, 2022

(54) IMAGING APPARATUS AND RECORDING MEDIUM OPERATING IN A FIRST MODE OR A SECOND MODE BASED ON DETERMINED BRIGHTNESS OF AN IMAGE

(71) Applicant: OLYMPUS CORPORATION, Hachioji (JP)

(72) Inventor: Takuya Totsuka, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 17/370,669

(22) Filed: Jul. 8, 2021

(65) Prior Publication Data

US 2021/0337132 A1 Oct. 28, 2021

Related U.S. Application Data

(63) Continuation of application No. PCT/JP2019/004433, filed on Feb. 7, 2019.

(51) Int. Cl.
*H04N 5/232* (2006.01)
*H04N 5/235* (2006.01)
*H04N 5/225* (2006.01)

(52) U.S. Cl.
CPC ..... *H04N 5/232411* (2018.08); *H04N 5/2351* (2013.01); *H04N 2005/2255* (2013.01)

(58) Field of Classification Search
CPC ........... H04N 5/232411; H04N 5/2351; H04N 2005/2255; H04N 5/23203; H04N 5/23245; A61B 1/00; G03B 7/093; G03B 7/26; G03B 17/02
See application file for complete search history.

(56) References Cited

U.S. PATENT DOCUMENTS

| | | | |
|---|---|---|---|
| 2008/0158348 A1* | 7/2008 | Karpen | A61B 1/00036 348/82 |
| 2011/0063475 A1* | 3/2011 | Kashiwagi | H04N 5/3728 348/229.1 |
| 2019/0174043 A1* | 6/2019 | Wang | H04N 5/238 |

FOREIGN PATENT DOCUMENTS

| | | |
|---|---|---|
| EP | 2 255 717 A1 | 12/2010 |
| JP | 61-62438 A | 3/1986 |
| JP | 10-243385 A | 9/1998 |
| JP | 2005-20130 A | 1/2005 |
| JP | 2005-80694 A | 3/2005 |
| JP | 2005-80843 A | 3/2005 |

(Continued)

OTHER PUBLICATIONS

International Search Report dated May 14, 2019, issued in counterpart International Application No. PCT/JP2019/004433, with English Translation. (4 pages).

*Primary Examiner* — Luong T Nguyen
(74) *Attorney, Agent, or Firm* — WHDA, LLP

(57) ABSTRACT

An imaging apparatus includes an imaging device and a processor. The processor is configured to determine brightness of an image when the imaging apparatus is operating in a second operation mode. The processor is configured to increase imaging sensitivity of the imaging device when the processor determines that the brightness is darker than or equal to a first brightness. The processor is configured to cause the imaging apparatus to operate in a first operation mode when the processor determines that the brightness is darker than or equal to a second brightness darker than the first brightness after the processor increases the imaging sensitivity.

11 Claims, 15 Drawing Sheets

(56) References Cited

FOREIGN PATENT DOCUMENTS

| | | | |
|---|---|---|---|
| JP | 2009-226065 A | 10/2009 |
| JP | 2010-184054 A | 8/2010 |

\* cited by examiner

IMAGING APPARATUS AND RECORDING MEDIUM OPERATING IN A FIRST MODE OR A SECOND MODE BASED ON DETERMINED BRIGHTNESS OF AN IMAGE The present application is a continuation application based on International Patent Application No. PCT/JP2019/004433 filed on Feb. 7, 2019, the content of which is incorporated herein by reference.

BACKGROUND OF THE INVENTION

Field of the Invention

The present invention relates to an imaging apparatus and a recording medium.

Description of Related Art

Wireless endoscopes operating with batteries have been developed in recent years. As the battery capacity increases, the weight of a wireless endoscope increases. Therefore, portability is lost. Thus, it is desirable that a wireless endoscope does not waste power.

Japanese Unexamined Patent Application, First Publication No. 2005-080694 discloses a technology of suppressing the power consumption of a capsule endoscope. The capsule endoscope disclosed in Japanese Unexamined Patent Application, First Publication No. 2005-080694 determines whether or not the capsule endoscope has been taken inside a subject by using the following method. After the capsule endoscope is activated, the capsule endoscope detects the brightness of an image acquired by an imaging apparatus. When the brightness of the image is less than or equal to a predetermined value, the capsule endoscope determines that the capsule endoscope has been taken inside a subject. Thereafter, the capsule endoscope starts supplying a light source, a wireless device, and the like with electric power.

SUMMARY OF THE INVENTION

According to a first aspect of the present invention, an imaging apparatus is configured to operate in any one of a first operation mode and a second operation mode. An amount of power consumption in the second operation mode is less than an amount of power consumption in the first operation mode. The imaging apparatus includes an imaging device and a processor. The imaging device is configured to generate an image. The processor is configured to determine brightness of the image when the imaging apparatus is operating in the second operation mode. The processor is configured to increase imaging sensitivity of the imaging device when the processor determines that the brightness is darker than or equal to a first brightness. The processor is configured to cause the imaging apparatus to operate in the first operation mode when the processor determines that the brightness is darker than or equal to a second brightness darker than the first brightness after the processor increases the imaging sensitivity.

According to a second aspect of the present invention, in the first aspect, the processor may be configured to increase the imaging sensitivity by lengthening an exposure time of the imaging device.

According to a third aspect of the present invention, in the first aspect, the processor may be configured to increase the imaging sensitivity by increasing gain of the imaging device.

According to a fourth aspect of the present invention, in the first aspect, the processor may be configured to change the imaging sensitivity to a first imaging sensitivity by increasing the imaging sensitivity when the processor determines that the brightness is darker than or equal to the first brightness and is brighter than a third brightness. The third brightness may be brighter than the second brightness and may be darker than the first brightness. The processor may be configured to change the imaging sensitivity to a second imaging sensitivity by increasing the imaging sensitivity when the processor determines that the brightness is darker than or equal to the third brightness. The second imaging sensitivity may be higher than the first imaging sensitivity.

According to a fifth aspect of the present invention, in the fourth aspect, the third brightness when the imaging sensitivity is the first imaging sensitivity may be darker than the third brightness when the imaging sensitivity is the second imaging sensitivity.

According to a sixth aspect of the present invention, in any one of the first to fifth aspects, the processor may be configured to determine that the imaging device is inserted into an observation target when the brightness is darker than or equal to the second brightness.

According to a seventh aspect of the present invention, in the first aspect, the processor may be configured to cause the imaging apparatus to operate in the first operation mode when the processor determines that the brightness is darker than or equal to a third brightness. The third brightness may be darker than the first brightness. The processor may be configured to increase the imaging sensitivity when the processor determines that the brightness is darker than or equal to the first brightness and is brighter than the third brightness.

According to an eighth aspect of the present invention, in the seventh aspect, the third brightness may be darker than the second brightness.

According to a ninth aspect of the present invention, in the first aspect, the processor may be configured to cause the imaging apparatus to operate in the second operation mode after the imaging apparatus starts to operate in the first operation mode. The processor may be configured to cause the imaging apparatus to operate in the first operation mode when the processor determines that the brightness is darker than or equal to a third brightness after an operation mode of the imaging apparatus is changed from the first operation mode to the second operation mode. The third brightness may be darker than the first brightness. The processor may be configured to increase the imaging sensitivity when the processor determines that the brightness is brighter than the third brightness and is darker than or equal to the first brightness after the operation mode of the imaging apparatus is changed from the first operation mode to the second operation mode.

According to a tenth aspect of the present invention, in the ninth aspect, the third brightness may be darker than the second brightness.

According to an eleventh aspect of the present invention, a non-transitory computer-readable recording medium saves a program for causing a processor of an imaging apparatus to execute a first step, a second step, and a third step. The imaging apparatus is configured to operate in any one of a first operation mode and a second operation mode wherein an amount of power consumption in the second operation mode is less than an amount of power consumption in the first operation mode. The processor determines brightness of an image generated by an imaging device in the first step when the imaging apparatus is operating in the second operation mode. The processor increases imaging sensitivity of the imaging device in the second step when the processor determines that the brightness is darker than or equal to a first brightness. The processor causes the imaging apparatus to operate in the first operation mode in the third step when the processor determines that the brightness is darker than or equal to a second brightness darker than the first brightness after the processor increases the imaging sensitivity.

DETAILED DESCRIPTION OF THE INVENTION

Hereinafter, embodiments of the present invention will be described with reference to the drawings.

First Embodiment

Figure 1:
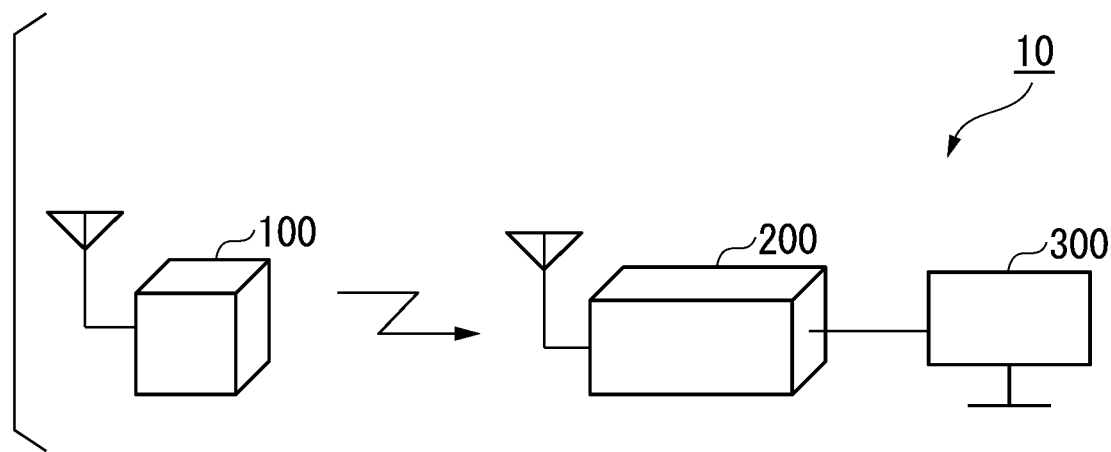
FIG. 1 is a block diagram showing a configuration of a wireless endoscope system according to a first embodiment of the present invention.

FIG. 1 shows a configuration of a wireless endoscope system 10 according to a first embodiment of the present invention. The wireless endoscope system 10 shown in FIG. 1 includes a transmission terminal 100, a reception terminal 200, and a monitor 300 (display). The transmission terminal 100 is to be inserted into an observation target. The transmission terminal 100 and the reception terminal 200 perform wireless communication. The reception terminal 200 is connected to the monitor 300 by a cable or the like. For example, the monitor 300 is constituted by a liquid crystal display device and a control circuit thereof. The reception terminal 200 and the monitor 300 may be integrated together.

Figure 2:
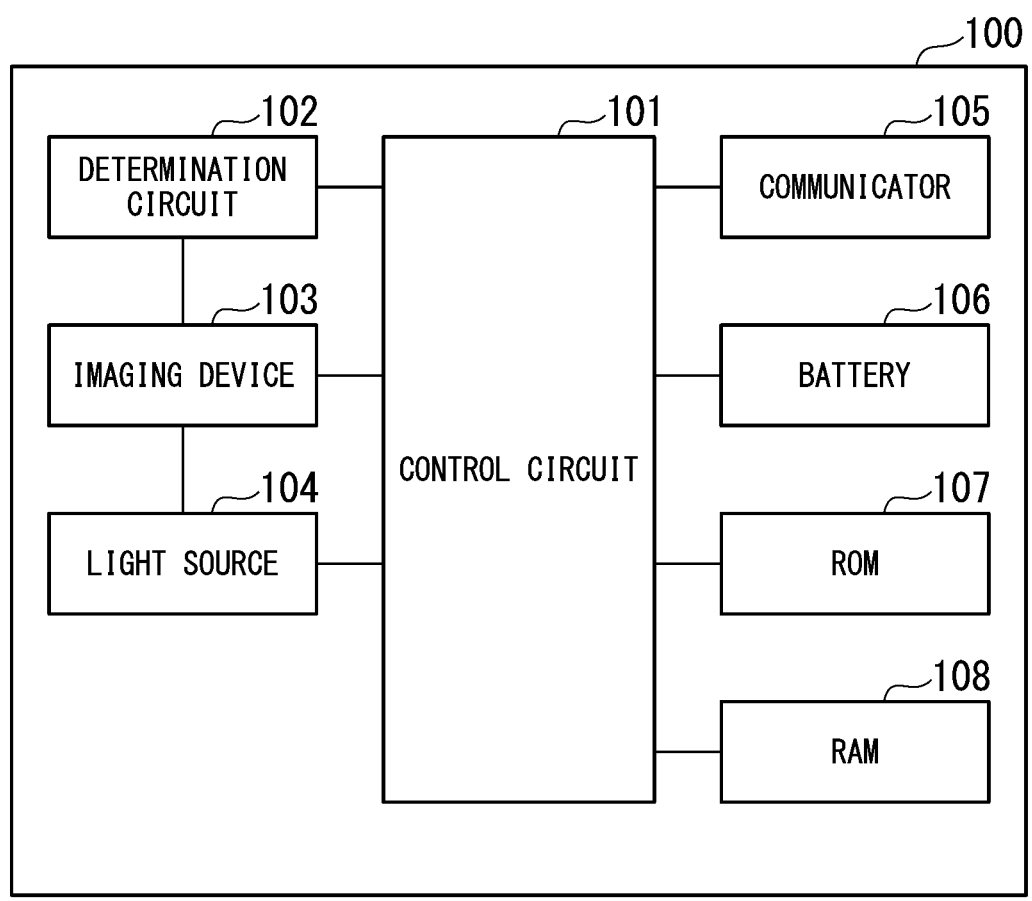
FIG. 2 is a block diagram showing a configuration of a transmission terminal according to the first embodiment of the present invention.

FIG. 2 shows a configuration of the transmission terminal 100. The transmission terminal 100 is an imaging apparatus. The transmission terminal 100 shown in FIG. 1 includes a control circuit 101, a determination circuit 102, an imaging device 103, a light source 104, a communicator 105, a battery 106, a ROM 107, and a RAM 108.

A schematic configuration of the transmission terminal 100 will be described. The transmission terminal 100 operates in any one of a normal mode (first operation mode) and a power-saving mode (second operation mode). The amount of power consumption in the power-saving mode is less than the amount of power consumption in the normal mode. The imaging device 103 generates an image. The determination circuit 102 determines the brightness of the image when the transmission terminal 100 is operating in the power-saving mode. The control circuit 101 increases the imaging sensitivity of the imaging device 103 when the determination circuit 102 determines that the brightness of the image is darker than or equal to a first brightness. The control circuit 101 causes the transmission terminal 100 to operate in the normal mode when the determination circuit 102 determines that the brightness of the image is darker than or equal to a second brightness darker than the first brightness after the control circuit 101 increases the imaging sensitivity of the imaging device 103.

A detailed configuration of the transmission terminal 100 will be described. The control circuit 101 (controller) controls power consumption of a control target. The control target is at least one of the imaging device 103, the light source 104, and the communicator 105. The control target may be any one of the imaging device 103, the light source 104, and the communicator 105. The control target may be any two of the imaging device 103, the light source 104, and the communicator 105. The control target may be all of the imaging device 103, the light source 104, and the communicator 105. When the control circuit 101 causes the transmission terminal 100 to operate in the normal mode, the control circuit 101 makes power consumption of the control target greater than that in the power-saving mode.

The operation mode of the transmission terminal 100 is any one of the normal mode and the power-saving mode. In the normal mode, the transmission terminal 100 executes a normal function for observation. In the power-saving mode, the transmission terminal 100 does not execute the normal function and the electric power supply is reduced.

The imaging device 103 is to be inserted into an observation target including space. For example, the observation target is the nasal cavity, the oral cavity, the ear, the throat, the stomach, the duodenum, the gallbladder, the pancreas, the small intestine, the large intestine, the appendix, the anus, a blood vessel, the brain, a joint, a bone, the urethra, the bladder, the liver, the kidney, a genital organ, or the diaphragm. The observation target may be a portion in a living body other than the above-described examples. In a case in which a plurality of portions are connected to each other, the space is the inside of any one of the plurality of portions and the outside is the outside of the plurality of portions. The observation target is not limited to the portion in the living body. The observation target may be an engine, a tubular pipe, a water pipe, or the like. For example, the entrance of the space and the exit of the space are the same. The imaging device 103 is inserted into the space through the entrance of the space. The imaging device 103 goes out of the space through the exit of the space. For example, an object surrounding the space is a tubular wall surface. The imaging device 103 images the object and generates an image of the object.

The imaging device 103 is an image sensor (imager). For example, the imaging device 103 is a CCD or CMOS sensor. The imaging device 103 transforms light incident to the imaging device 103 into an electric signal, that is, an imaging signal. The analog imaging signal is converted into a digital signal, that is, image data by an analog-to-digital converter (AD converter). In other words, the imaging device 103 images a subject and generates image data. The imaging device 103 images the subject in every imaging cycle and generates image data of each frame. The imaging device 103 outputs the image data to the control circuit 101 and the determination circuit 102. For example, the imaging sensitivity of the imaging device 103 can be expressed as a ratio of a signal value of the image to the amount of light incident to the imaging device 103.

The determination circuit 102 determines the brightness of the image output from the imaging device 103. For example, the determination circuit 102 calculates an average value of all or some of the plurality of pixel values included in the image data and determines the brightness of the image on the basis of the average value. The determination circuit 102 may calculate a brightness value of the image and may determine the brightness of the image on the basis of the brightness value. The determination circuit 102 determines whether or not the imaging device 103 is inserted into the observation target on the basis of the brightness of the image. The determination circuit 102 outputs a determination result to the control circuit 101.

For example, the light source 104 is a light-emitting diode (LED). The light source 104 generates illumination light. The light source 104 emits the illumination light to the space in the observation target into which the transmission terminal 100 is to be inserted. The light source 104 illuminates the range imaged by the imaging device 103 by emitting the illumination light.

The communicator 105 (transmitter) is a wireless communicator. The communicator 105 includes an antenna. Alternatively, the communicator 105 is connected to the antenna. The communicator 105 performs wireless communication with the reception terminal 200. The communicator 105 transmits the image data to the reception terminal 200 by radio.

The battery 106 supplies electric power to the control circuit 101, the determination circuit 102, the imaging device 103, the light source 104, the communicator 105, the ROM 107, and the RAM 108.

The ROM 107 is a nonvolatile memory such as a flash ROM. Program data and various kinds of setting information are stored on the ROM 107. The program data are used for controlling the transmission terminal 100. The setting information includes a communication-setting parameter. The RAM 108 is a volatile memory. The RAM 108 is used as a buffer, a work area, and a temporary area. The buffer is used for temporarily storing image data. The work area is used for operations or the like executed by the control circuit 101. The temporary area is used for temporarily storing various kinds of setting information or the like.

For example, in the normal mode, the control circuit 101 may increase the imaging rate of the imaging device 103, thereby making it greater than that in the power-saving mode. In the normal mode, the control circuit 101 may increase the resolution of the image data generated by the imaging device 103, thereby making it greater than that in the power-saving mode. In the normal mode, the control circuit 101 may increase the amount of the irradiation light of the light source 104, thereby making it greater than that in the power-saving mode. In the normal mode, the control circuit 101 may increase the transmission rate of the communicator 105, thereby making it greater than that in the power-saving mode.

In the power-saving mode, the control circuit 101 may turn off the power source of the control target except for the control circuit 101, the determination circuit 102, and the imaging device 103. In this case, the control circuit 101 causes the battery 106 to stop supply of electric power to the control target except for the control circuit 101, the determination circuit 102, and the imaging device 103. The light source 104 may be turned off in the power-saving mode and may be turned on in the normal mode. The communicator 105 may stop communication in the power-saving mode and may perform communication in the normal mode.

The control circuit 101 outputs the image data output from the imaging device 103 to the communicator 105. The image data may be compressed. In the normal mode, the control circuit 101 may increase the compression rate of the image data, thereby making it greater than that in the power-saving mode. The control circuit 101 does not need to compress the image data in the power-saving mode and may compress the image data in the normal mode.

The control circuit 101 and the determination circuit 102 are constituted by at least one of a processor and a logic circuit. For example, the processor is at least one of a central processing unit (CPU), a digital signal processor (DSP), and a graphics-processing unit (GPU). For example, the logic circuit is at least one of an application-specific integrated circuit (ASIC) and a field-programmable gate array (FPGA). The control circuit 101 and the determination circuit 102 may include one or a plurality of processors. The control circuit 101 and the determination circuit 102 may include one or a plurality of logic circuits. The control circuit 101 and the determination circuit 102 operate in accordance with a program stored on the ROM 107.

The processor may read and execute a program. The program includes commands defining the operations of the control circuit 101 and the determination circuit 102. In other words, the functions of the control circuit 101 and the determination circuit 102 can be realized as software. The program, for example, may be provided by using a "computer-readable storage medium" such as a flash memory. The program may be transmitted from a computer storing the program to the transmission terminal 100 through a transmission medium or by using carrier waves in a transmission medium. The "transmission medium" transmitting a program is a medium that has a function of transmitting information. The medium that has a function of transmitting information includes a network (communication network) including the Internet and the like or a communication circuit line (communication line) including a telephone circuit line and the like. The program described above may realize at least some of the functions described above. Furthermore, the program described above may be a differential file (differential program). The functions described above may be realized by a combination of a differential program and a program that has already been recorded in a computer.

The control circuit 101 transmits the image data to the reception terminal 200 by using the communicator 105. Specifically, the control circuit 101 controls the communicator 105 such that the image data are transmitted to the reception terminal 200. In other words, the control circuit 101 causes the communicator 105 to transmit the image data for the reception terminal 200. In this way, the communicator 105 transmits the image data to the reception terminal 200.

Figure 3:
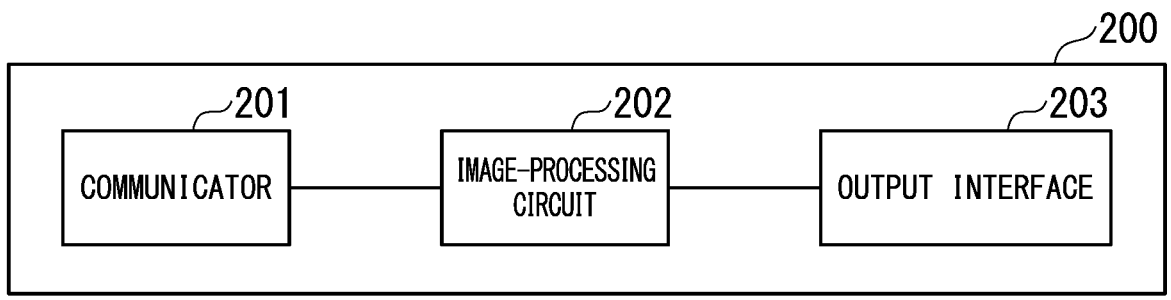
FIG. 3 is a block diagram showing a configuration of a reception terminal according to the first embodiment of the present invention.

FIG. 3 shows a configuration of the reception terminal 200. The reception terminal 200 shown in FIG. 3 includes a communicator 201, an image-processing circuit 202, and an output interface 203.

The communicator 201 (receiver) is a wireless communicator. The communicator 201 includes an antenna. Alternatively, the communicator 201 is connected to the antenna. The communicator 201 performs wireless communication with the transmission terminal 100. The communicator 201 receives the image data from the transmission terminal 100 by radio. The communicator 201 outputs the received image data to the image-processing circuit 202.

The image-processing circuit 202 performs image processing on the image data received by the communicator 201. For example, the image-processing circuit 202 converts the image data into display data in a format used for displaying an image. In a case in which the image data are compressed, the image-processing circuit 202 may expand the image data. The image-processing circuit 202 outputs the display data to the output interface 203.

The output interface 203 is connected to the monitor 300. The output interface 203 outputs the display data output from the image-processing circuit 202 to the monitor 300. The monitor 300 displays an image on the basis of the display data.

The transmission terminal 100 and the reception terminal 200 may be connected together by a cable. In this case, the communicator 105 and the communicator 201 are connected together by the cable. The communicator 105 and the communicator 201 perform communication via the cable.

Figure 4:
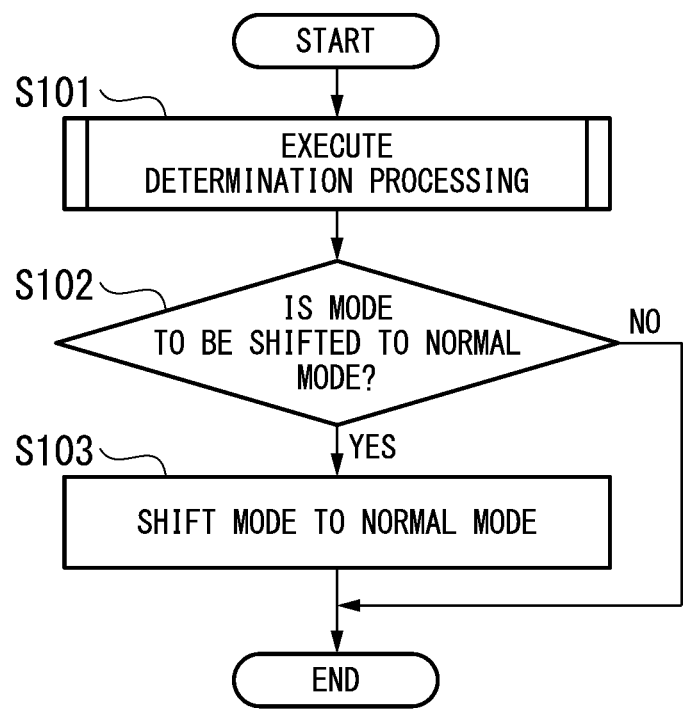
FIG. 4 is a flow chart showing a procedure of an operation of the transmission terminal according to the first embodiment of the present invention.

FIG. 4 shows a procedure of an operation of the transmission terminal 100 in the power-saving mode. The operation of the transmission terminal 100 will be described with reference to FIG. 4. For example, immediately after the power source of the transmission terminal 100 is turned on, the transmission terminal 100 operates in the power-saving mode.

The transmission terminal 100 executes determination processing (Step S101). In the determination processing, the determination circuit 102 determines whether or not the imaging device 103 is inserted into the observation target. Details of the determination processing will be described later.

After Step S101, the control circuit 101 determines whether or not to shift the operation mode to the normal mode on the basis of the result of the determination processing (Step S102). When the determination circuit 102 determines that the imaging device 103 is inserted into the observation target in the determination processing, the control circuit 101 determines to shift the operation mode to the normal mode. When the determination circuit 102 determines that the imaging device 103 has not been inserted into the observation target in the determination processing, the control circuit 101 determines not to shift the operation mode to the normal mode.

When the control circuit 101 determines to shift the operation mode to the normal mode in Step S101, the control circuit 101 causes the transmission terminal 100 to operate in the normal mode (Step S103). In this way, the processing shown in FIG. 4 is completed. When the control circuit 101 determines not to shift the operation mode to the normal mode in Step S101, the processing shown in FIG. 4 is completed. While the transmission terminal 100 operates in the power-saving mode, the processing shown in FIG. 4 is repeatedly executed.

The control circuit 101 increases the power consumption of the control target in Step S103, thereby making it greater than that in the power-saving mode. The control circuit 101 changes the mode of the transmission terminal 100 from the power-saving mode to the normal mode in Step S103. Mode information indicating the normal mode is stored on the RAM 108.

While the normal mode is set to the transmission terminal 100, the imaging device 103 periodically images an object in the space. While the normal mode is set to the transmission terminal 100, the light source 104 generates illumination light and emits the illumination light to the object in the space. While the normal mode is set to the transmission terminal 100, the communicator 105 periodically transmits image data to the reception terminal 200.

Figure 5:
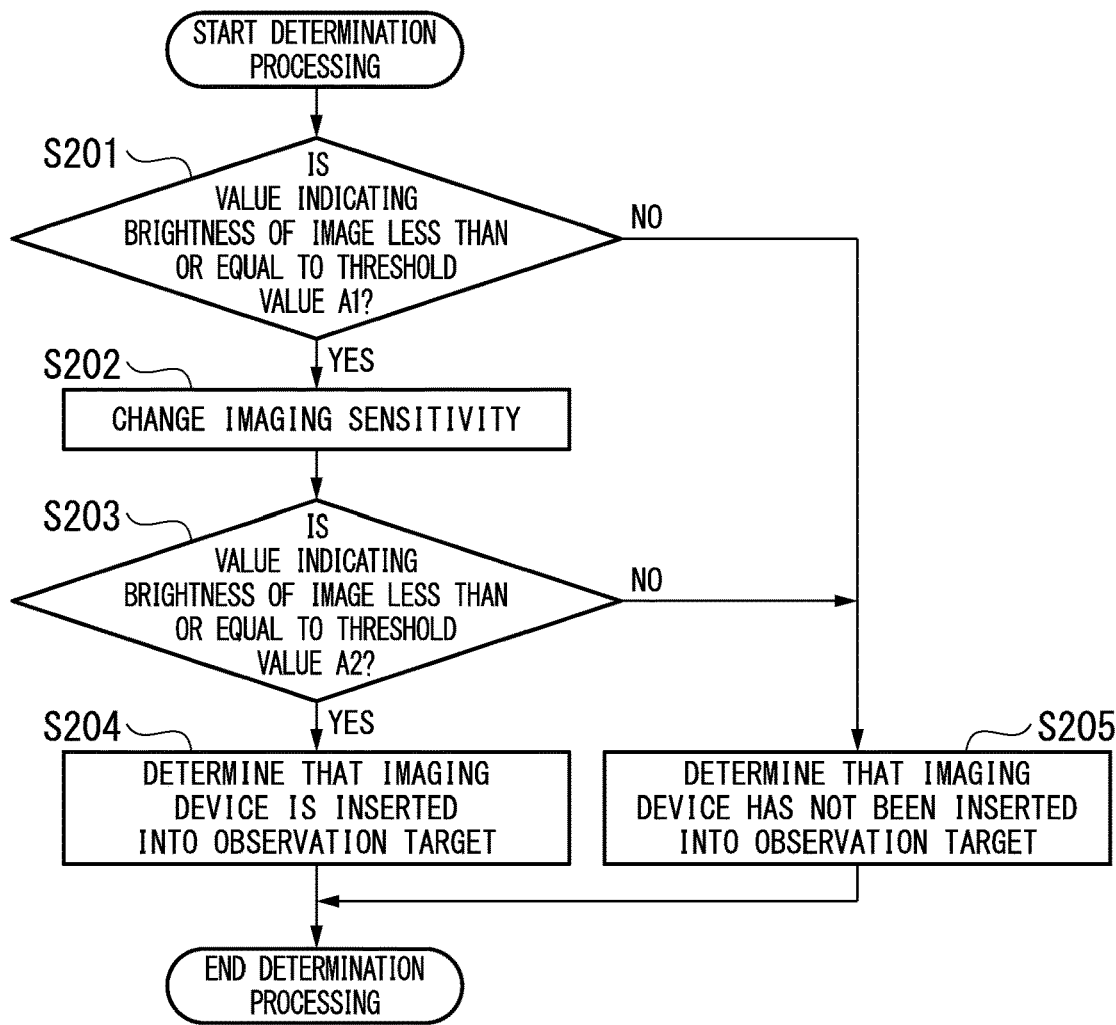
FIG. 5 is a flow chart showing a procedure of an operation of the transmission terminal according to the first embodiment of the present invention.

FIG. 5 shows details of the determination processing in Step S101. An operation of the transmission terminal 100 in the determination processing will be described with reference to FIG. 5.

The determination circuit 102 detects the brightness of the image output from the imaging device 103 and determines whether or not the value indicating the brightness is less than or equal to a threshold value A1 (Step S201). The threshold value A1 indicates the first brightness. For example, the threshold value A1 is experimentally decided.

When the determination circuit 102 determines that the value indicating the brightness of the image is less than or equal to the threshold value A1 in Step S201, the determination circuit 102 outputs a determination result to the control circuit 101. The control circuit 101 changes the imaging sensitivity of the imaging device 103 on the basis of the determination result (Step S202).

For example, the control circuit 101 increases the imaging sensitivity by lengthening the exposure time of the imaging device 103 in Step S202. The exposure time after Step S202 is executed is longer than that before Step S202 is executed. Alternatively, the control circuit 101 increases the imaging sensitivity by increasing the gain of the imaging device 103 in Step S202. The gain after Step S202 is executed is greater than that before Step S202 is executed.

Methods other than the method of changing the imaging sensitivity of the imaging device 103 may be used. For example, the determination circuit 102 may add values of a plurality of pixels in the image data together in Step S202, thereby increasing the value of each pixel. The determination circuit 102 determines the brightness of the image on the basis of the added value. Any one of the plurality of methods described above may be used. The plurality of methods described above may be simultaneously used.

Before the imaging device 103 is inserted into the observation target, the operation mode of the transmission terminal 100 is the power-saving mode. In a case in which the determination circuit 102 determines that the value indicating the brightness of the image is less than or equal to the threshold value A1 in Step S201, there is a possibility that the imaging device 103 is inserted into the observation target. Alternatively, there is a possibility that the imaging device 103 is not inserted into the observation target and is used in a dark place outside the observation target. In order to determine whether the imaging device 103 is inserted into the observation target or is used in a dark place outside the observation target, the control circuit 101 increases the imaging sensitivity of the imaging device 103 in Step S202. When the imaging sensitivity of the imaging device 103 increases, the power consumption of the imaging device 103 increases. In order to suppress the power consumption of the imaging device 103, the control circuit 101 increases the imaging sensitivity of the imaging device 103 only when the image becomes dark to some extent. The power consumption of the transmission terminal 100 after the imaging sensitivity of the imaging device 103 increases is less than that in the normal mode.

Since the processing shown in FIG. 4 is repeatedly executed, the processing shown in FIG. 5 is repeatedly executed. In a case in which Step S202 has been executed more than once and the imaging sensitivity of the imaging device 103 has already been changed, Step S202 is not executed and Step S203 is executed.

After Step S202, the determination circuit 102 detects the brightness of the image output from the imaging device 103 and determines whether or not the value indicating the brightness is less than or equal to a threshold value A2 (Step S203). The threshold value A2 indicates the second brightness. The threshold value A2 is less than the threshold value A1. For example, the threshold value A2 is experimentally decided. The image generated by the imaging device 103 after Step S102 is executed is used in Step S203.

When the determination circuit 102 determines that the value indicating the brightness of the image is less than or equal to the threshold value A2 in Step S203, the determination circuit 102 determines that the imaging device 103 is inserted into the observation target. The determination circuit 102 outputs a determination result to the control circuit 101 (Step S204). When the Step S204 is executed, the determination processing is completed.

When the determination circuit 102 determines that the value indicating the brightness of the image is greater than the threshold value A1 in Step S201, the determination circuit 102 determines that the imaging device 103 is not inserted into the observation target. When the determination circuit 102 determines that the value indicating the brightness of the image is greater than the threshold value A2 in Step S203, the determination circuit 102 also determines that the imaging device 103 is not inserted into the observation target. The determination circuit 102 outputs the determination result to the control circuit 101 (Step S205). When the Step S205 is executed, the determination processing is completed.

There is a possibility that the imaging device 103 is inserted into the observation target when the transmission terminal 100 is operating in the power-saving mode. In order to correctly detect the brightness around the transmission terminal 100, the amount of irradiation light of the light source 104 in the power-saving mode is set such that a dark image is acquired even when the imaging device 103 is inserted into the observation target.

After the control circuit 101 increases the imaging sensitivity of the imaging device 103, the image used in Step S203 is acquired. In a case in which the imaging rate in the power-saving mode is low, the control circuit 101 may temporarily increase the imaging rate of the imaging device 103 in order to quickly execute the determination in Step S203. After Step S203, the control circuit 101 restores the imaging rate of the imaging device 103 to that in the power-saving mode.

An image compression method in which darker images have higher compression rates may be used. In a case in which the method is used, the determination circuit 102 may acquire information of the compression rate from the control circuit 101 and may determine the brightness of an image on the basis of the compression rate.

FIGS. 6 to 9 show the change in the brightness of an image. The horizontal axis of the graph shown in each drawing indicates time, and the vertical axis of the graph shown in each drawing indicates the brightness of an image.

Figure 6:
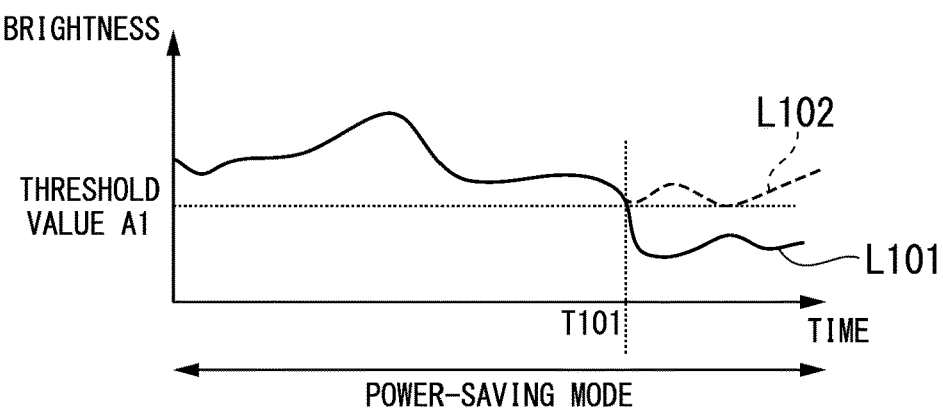
FIG. 6 is a graph showing the change in the brightness of an image in the first embodiment of the present invention.

In FIG. 6, the value indicating the brightness of an image generated before a time point T101 is greater than the threshold value A1. Therefore, the determination circuit 102 determines that the imaging device 103 is not inserted into the observation target. The operation mode of the transmission terminal 100 is maintained in the power-saving mode until the time point T101. The value indicating the brightness of an image generated at the time point T101 is less than or equal to the threshold value A1. Therefore, the control circuit 101 increases the imaging sensitivity of the imaging device 103. In a case in which the imaging device 103 is used in a very dark place, the image becomes dark, as the line L101 shows. In a case in which the imaging device 103 is used in a slightly dark place, the image may become bright due to the increase in the imaging sensitivity, as the line L102 shows. The operation mode of the transmission terminal 100 is maintained in the power-saving mode even after the time point T101.

Figure 7:
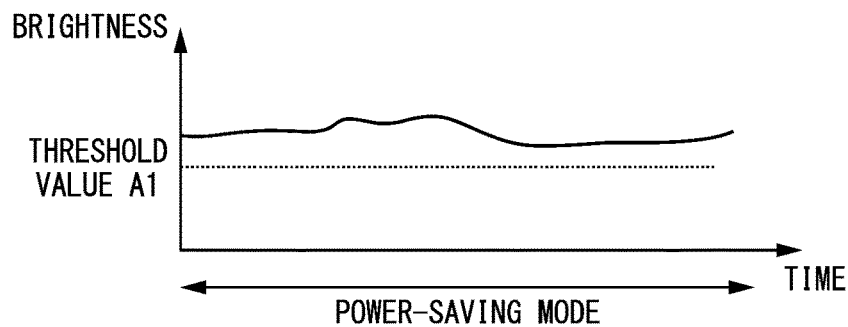
FIG. 7 is a graph showing the change in the brightness of an image in the first embodiment of the present invention.

In FIG. 7, the brightness of an image is always greater than the threshold value A1. Therefore, the determination circuit 102 determines that the imaging device 103 is not inserted into the observation target. The operation mode of the transmission terminal 100 is maintained in the power-saving mode.

Figure 8:
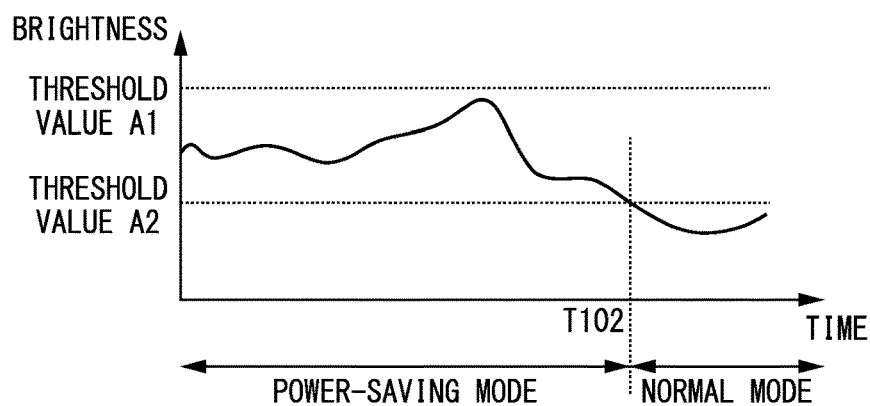
FIG. 8 is a graph showing the change in the brightness of an image in the first embodiment of the present invention.

FIG. 8 shows the change in the brightness of an image generated after the imaging sensitivity of the imaging device 103 increases. The value indicating the brightness of an image generated before a time point T102 is less than the threshold value A1 and is greater than the threshold value A2. Therefore, the determination circuit 102 determines that the imaging device 103 is not inserted into the observation target. The operation mode of the transmission terminal 100 is maintained in the power-saving mode until the time point T102. The value indicating the brightness of an image generated at the time point T102 is less than or equal to the threshold value A2. Therefore, the determination circuit 102 determines that the imaging device 103 is inserted into the observation target. The control circuit 101 changes the operation mode of the transmission terminal 100 to the normal mode.

Figure 9:
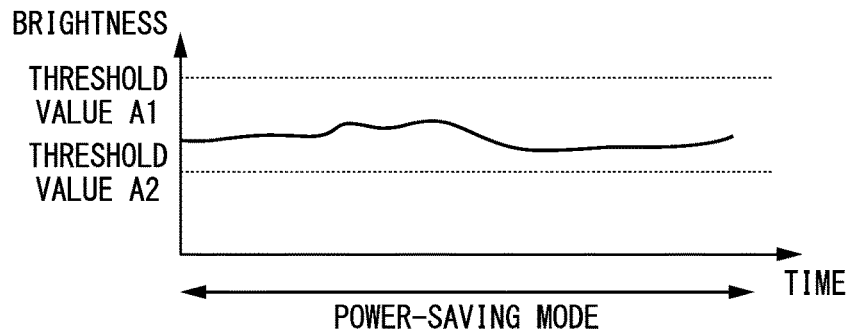
FIG. 9 is a graph showing the change in the brightness of an image in the first embodiment of the present invention.

FIG. 9 shows the change in the brightness of an image generated after the imaging sensitivity of the imaging device 103 increases. The brightness of an image is always less than the threshold value A1 and is greater than the threshold value A2. Therefore, the determination circuit 102 determines that the imaging device 103 is not inserted into the observation target. The operation mode of the transmission terminal 100 is maintained in the power-saving mode.

A program according to each aspect of the present invention causes the transmission terminal 100 to execute a first step (Step S201 and Step S203), a second step (Step S202), and a third step (Step S103).

The range to which an imaging apparatus according to each aspect of the present invention is applied is not limited to a wireless endoscope system. The range in which the imaging apparatus is used is not limited.

An imaging apparatus according to each aspect of the present invention does not need to include a communicator. Accordingly, the transmission terminal 100 does not need to include the communicator 105. In such a case, a control target of the power consumption is at least one of the imaging device 103 and the light source 104.

In the first embodiment, when the determination circuit 102 determines that the value indicating the brightness of an image is less than or equal to the threshold value A1, the control circuit 101 increases the imaging sensitivity of the imaging device 103. While the image is bright, the imaging sensitivity of the imaging device 103 is low. Therefore, the power consumption of the transmission terminal 100 is suppressed. After the control circuit 101 increases the imaging sensitivity of the imaging device 103, the control circuit 101 causes the transmission terminal 100 to operate in the normal mode when the determination circuit 102 determines that the value indicating the brightness of an image is less than or equal to the threshold value A2. Since the imaging sensitivity of the imaging device 103 increases, the transmission terminal 100 can correctly determine whether or not the imaging device 103 is inserted into the observation target.

First Modified Example of First Embodiment

Figure 10:
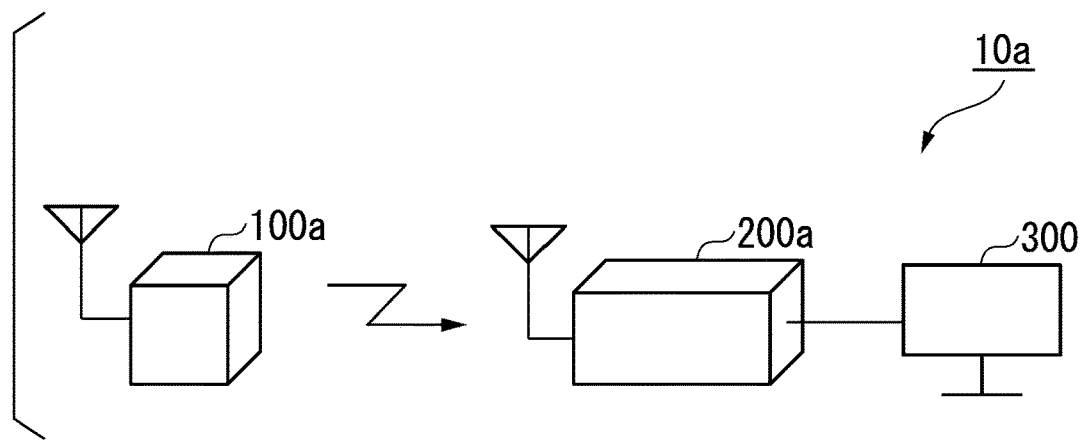
FIG. 10 is a block diagram showing a configuration of a wireless endoscope system according to a first modified example of the first embodiment of the present invention.

A first modified example of the first embodiment of the present invention will be described. FIG. 10 shows a configuration of a wireless endoscope system 10a according to the first modified example of the first embodiment of the present invention. The same configuration as that shown in FIG. 1 will not be described.

The wireless endoscope system 10a shown in FIG. 10 includes a transmission terminal 100a, a reception terminal 200a, and a monitor 300 (display). The wireless endoscope system 10a is an imaging apparatus. The transmission terminal 100 shown in FIG. 1 is changed to the transmission terminal 100a. The reception terminal 200 shown in FIG. 1 is changed to the reception terminal 200a.

Figure 11:
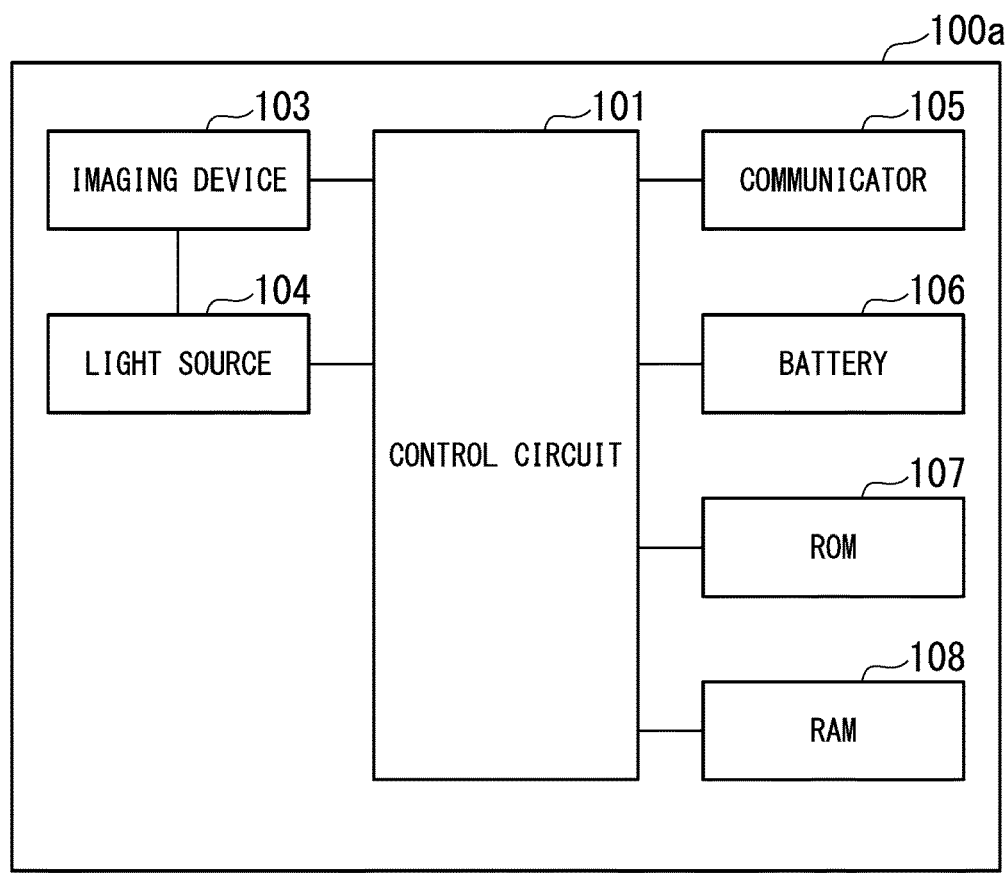
FIG. 11 is a block diagram showing a configuration of a transmission terminal according to the first modified example of the first embodiment of the present invention.

FIG. 11 shows a configuration of the transmission terminal 100a. The same configuration as that shown in FIG. 2 will not be described. The transmission terminal 100a shown in FIG. 11 includes a control circuit 101, an imaging device 103, a light source 104, a communicator 105, a battery 106, a ROM 107, and a RAM 108. The transmission terminal 100a does not include the determination circuit 102 shown in FIG. 2.

Figure 12:
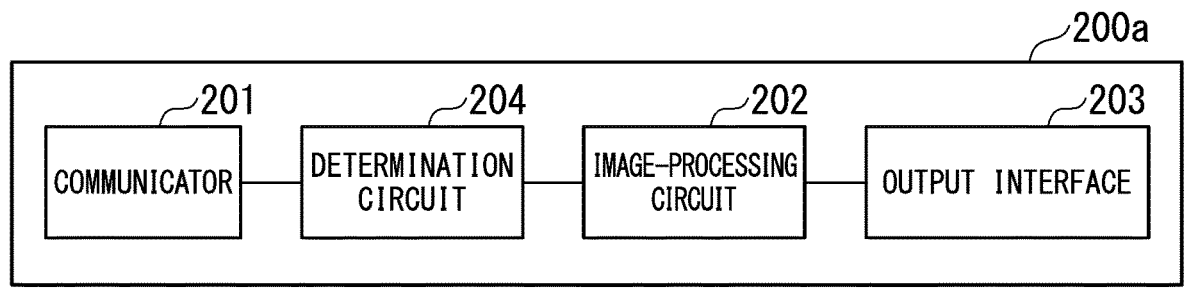
FIG. 12 is a block diagram showing a configuration of a reception terminal according to the first modified example of the first embodiment of the present invention.

FIG. 12 shows a configuration of the reception terminal 200a. The same configuration as that shown in FIG. 3 will not be described. The reception terminal 200a shown in FIG. 12 includes a communicator 201, an image-processing circuit 202, an output interface 203, and a determination circuit 204. The determination circuit 204 has a similar function to that of the determination circuit 102 shown in FIG. 2.

Figure 13:
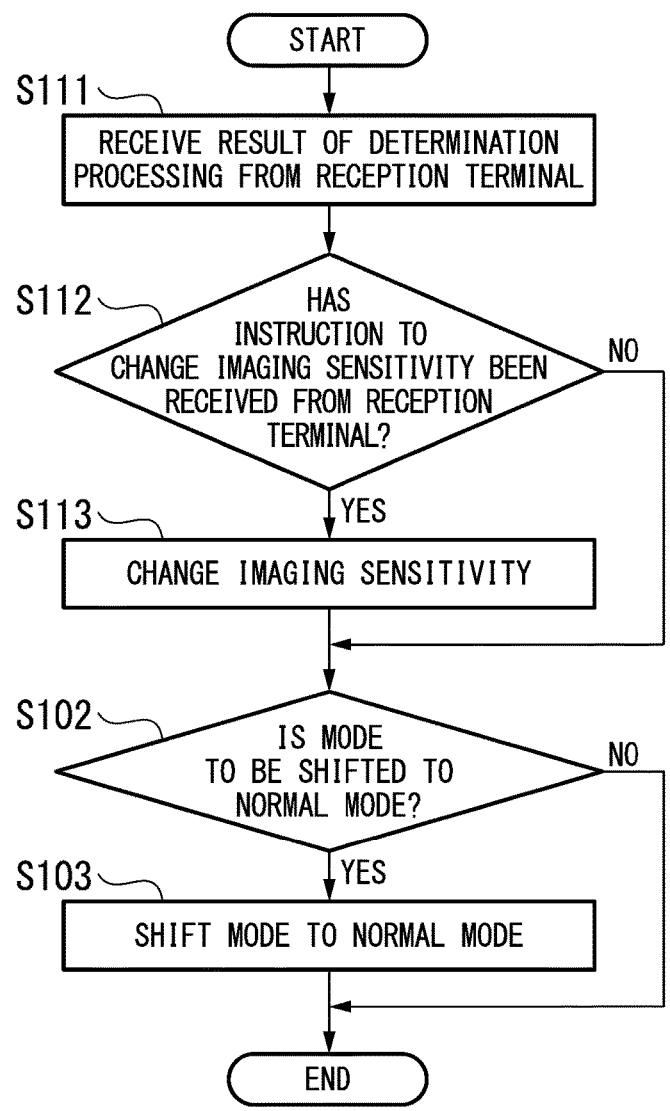
FIG. 13 is a flow chart showing a procedure of an operation of the transmission terminal according to the first modified example of the first embodiment of the present invention.

FIG. 13 shows a procedure of an operation of the transmission terminal 100a in the power-saving mode. The operation of the transmission terminal 100a will be described with reference to FIG. 13. The same processing as that shown in FIG. 4 will not be described. The communicator 105 periodically transmits image data to the reception terminal 200a to coincide with the processing shown in FIG. 13.

The communicator 105 receives a result of the determination processing executed by the determination circuit 204 from the reception terminal 200a. The communicator 105 outputs the received result of the determination processing to the control circuit 101 (Step S111).

After Step S111, the control circuit 101 determines whether or not an instruction to change the imaging sensitivity has been received from the reception terminal 200a (Step S112). The instruction to change the imaging sensitivity indicates increasing the imaging sensitivity of the imaging device 103.

When the control circuit 101 determines that the instruction to change the imaging sensitivity has not been received from the reception terminal 200a in Step S112, Step S102 is executed. When the control circuit 101 determines that the instruction to change the imaging sensitivity has been received from the reception terminal 200a in Step S112, the control circuit 101 changes the imaging sensitivity of the imaging device 103 on the basis of the instruction to change the imaging sensitivity (Step S113). After Step S113, Step S102 is executed.

Figure 14:
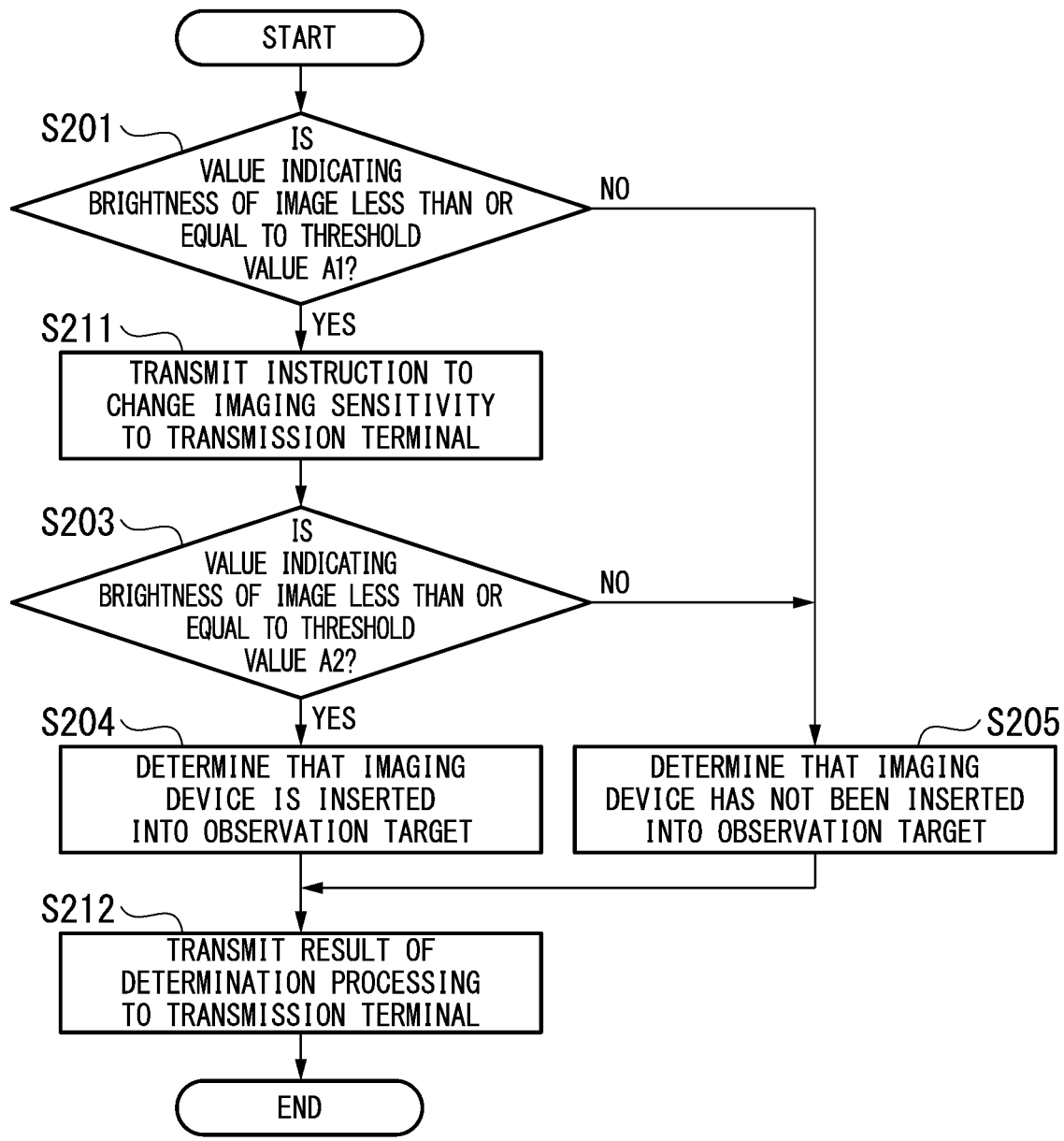
FIG. 14 is a flow chart showing a procedure of an operation of the reception terminal according to the first modified example of the first embodiment of the present invention.

FIG. 14 shows a procedure of an operation of the reception terminal 200a. The operation of the reception terminal 200a will be described with reference to FIG. 14. The same processing as that shown in FIG. 5 will not be described. The communicator 201 periodically receives image data from the transmission terminal 100a to coincide with the processing shown in FIG. 14.

Each of Step S201, Step S203, Step S204, and Step S205 is the same as the corresponding step shown in FIG. 5. Although the determination circuit 102 of the transmission terminal 100 executes Step S201, Step S203, Step S204, and Step S205 shown in FIG. 5, the determination circuit 204 of the reception terminal 200a executes Step S201, Step S203, Step S204, and Step S205 shown in FIG. 14.

When the determination circuit 204 determines that the value indicating the brightness of an image is less than or equal to the threshold value A1 in Step S201, the determination circuit 204 outputs the instruction to change the imaging sensitivity to the communicator 201. The communicator 201 transmits the instruction to change the imaging sensitivity to the transmission terminal 100a (Step S211). After Step S211, Step S203 is executed.

After Step S204 or Step S205, the determination circuit 204 outputs the result of the determination processing to the communicator 201. The communicator 201 transmits the result of the determination processing to the transmission terminal 100a (Step S212).

In the first modified example of the first embodiment, the power consumption of the transmission terminal 100a is suppressed. In addition, the reception terminal 200a can correctly determine whether or not the imaging device 103 is inserted into the observation target.

Second Modified Example of First Embodiment

A second modified example of the first embodiment of the present invention will be described. When the determination circuit 102 determines that the brightness of an image is darker than or equal to the first brightness and is brighter than a third brightness, the control circuit 101 changes the imaging sensitivity of the imaging device 103 to a first imaging sensitivity by increasing the imaging sensitivity. The third brightness is brighter than the second brightness and is darker than the first brightness. When the determination circuit 102 determines that the brightness of the image is darker than or equal to the third brightness, the control circuit 101 changes the imaging sensitivity of the imaging device 103 to a second imaging sensitivity by increasing the imaging sensitivity. The second imaging sensitivity is higher than the first imaging sensitivity.

Figure 15:
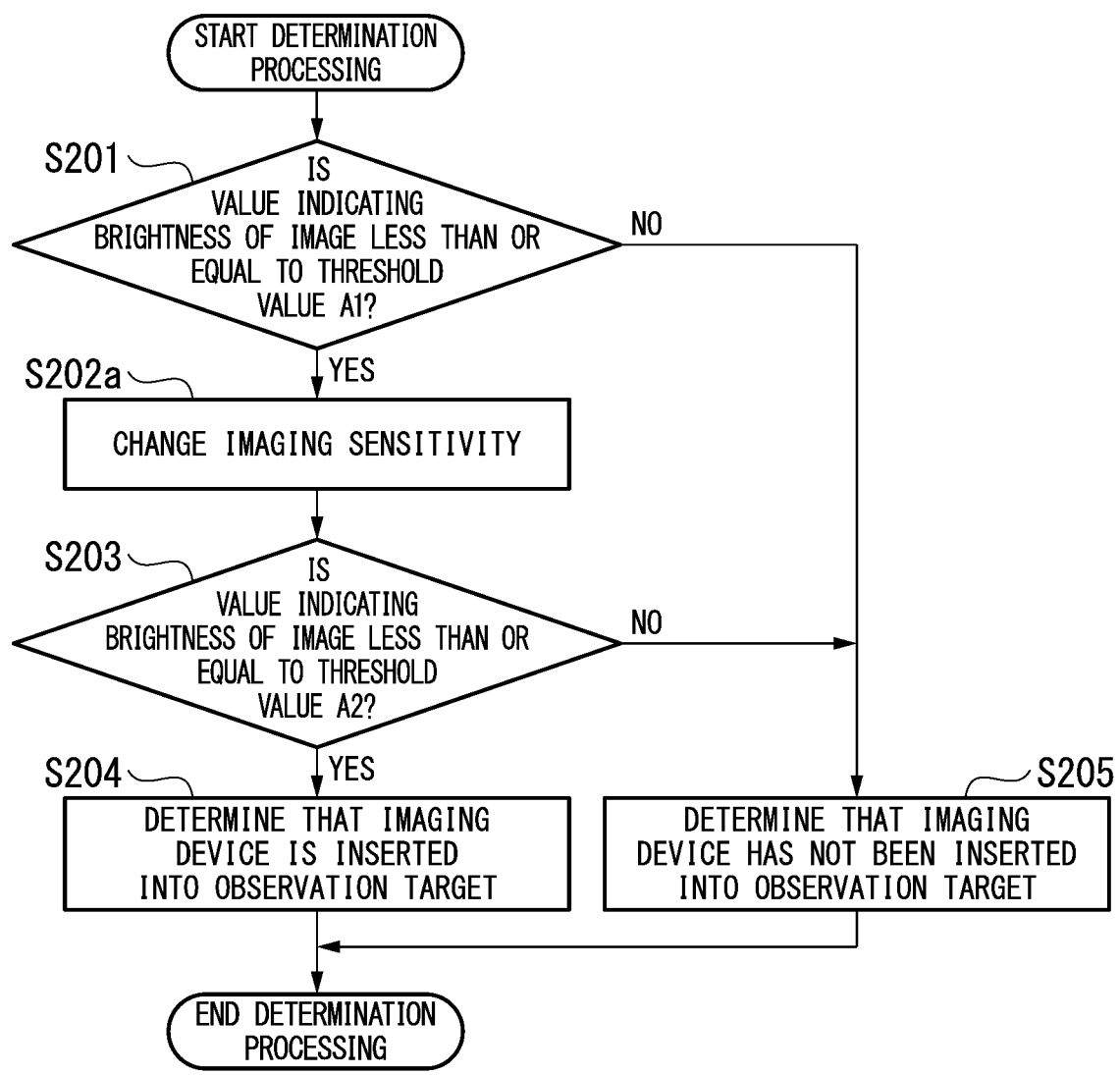
FIG. 15 is a flow chart showing a procedure of an operation of a transmission terminal according to a second modified example of the first embodiment of the present invention.

FIG. 15 shows details of the determination processing in Step S101 shown in FIG. 4. An operation of the transmission terminal 100 in the determination processing will be described with reference to FIG. 15. The same processing as that shown in FIG. 5 will not be described.

When the determination circuit 102 determines that the value indicating the brightness of the image is less than or equal to the threshold value A1 in Step S201, the determination circuit 102 outputs a determination result to the control circuit 101. The control circuit 101 changes the imaging sensitivity of the imaging device 103 on the basis of the determination result (Step S202a).

The control circuit 101 changes the imaging sensitivity on the basis of the value indicating the brightness of the image in Step S202a. For example, when the determination circuit 102 determines that the value indicating the brightness of the image is less than or equal to the threshold value A1 and is greater than a threshold value A3, the control circuit 101 changes the imaging sensitivity of the imaging device 103 to the first imaging sensitivity by increasing the imaging sensitivity. The threshold value A3 is greater than the threshold value A2 and is less than the threshold value A1. The threshold value A3 indicates the third brightness. The threshold value A3 is experimentally decided. When the determination circuit 102 determines that the value indicating the brightness of the image is less than or equal to the threshold value A3, the control circuit 101 changes the imaging sensitivity of the imaging device 103 to the second imaging sensitivity by increasing the imaging sensitivity.

For example, the control circuit 101 increases the imaging sensitivity by lengthening the exposure time of the imaging device 103 in Step S202a. For example, when the determination circuit 102 determines that the value indicating the brightness of the image is less than or equal to the threshold value A1 and is greater than the threshold value A3, the control circuit 101 changes the exposure time of the imaging device 103 to T1. The exposure time T1 is longer than the present exposure time. When the determination circuit 102 determines that the value indicating the brightness of the image is less than or equal to the threshold value A3, the control circuit 101 changes the exposure time of the imaging device 103 to T2. The exposure time T2 is longer than the exposure time T1.

Alternatively, the control circuit 101 increases the imaging sensitivity by increasing the gain of the imaging device 103 in Step S202a. For example, when the determination circuit 102 determines that the value indicating the brightness of the image is less than or equal to the threshold value A1 and is greater than the threshold value A3, the control circuit 101 changes the gain of the imaging device 103 to G1. The gain G1 is greater than the present gain. When the determination circuit 102 determines that the value indicating the brightness of the image is less than or equal to the threshold value A3, the control circuit 101 changes the gain of the imaging device 103 to G2. The gain G2 is greater than the gain G1.

In the above-described example, the imaging sensitivity of the imaging device 103 is changed to any one of the two imaging sensitivities in Step S202a. The imaging sensitivity of the imaging device 103 may be changed to any one of three or more imaging sensitivities in Step S202a. In such a case, two or more threshold values are set between the threshold value A1 and the threshold value A2.

Methods other than the method of changing the imaging sensitivity of the imaging device 103 may be used. For example, the determination circuit 102 may add values of a plurality of pixels in the image data together in Step S202a, thereby increasing the value of each pixel. For example, when the determination circuit 102 determines that the value indicating the brightness of the image is less than or equal to the threshold value A1 and is greater than the threshold value A3, the determination circuit 102 adds values of N1 pixels together. The number N1 is an integer greater than or equal to two. When the determination circuit 102 determines that the value indicating the brightness of the image is less than or equal to the threshold value A3, the determination circuit 102 adds values of N2 pixels together. The number N2 is greater than the number N1. The determination circuit 102 determines the brightness of the image on the basis of the added value.

In the above-described example, the number of pixels to be added is changed to any one of the two numbers in Step S202a. The number of pixels to be added may be changed to any one of three or more numbers in Step S202a.

Any one of the plurality of methods described above may be used. The plurality of methods described above may be simultaneously used.

There is a possibility that the brightness of an image changes in accordance with the change in the imaging sensitivity of the imaging device 103 even when the brightness around the transmission terminal 100 is fixed. After the imaging sensitivity of the imaging device 103 increases, the image tends to become brighter. Therefore, there is a possibility that the determination result of Step S203 in the first imaging sensitivity and the determination result of Step S203 in the second imaging sensitivity are different from each other. In light of this, the threshold value A2 in Step S203 may be changed in accordance with the imaging sensitivity that has been set in Step S202a.

For example, when the imaging sensitivity of the imaging device 103 is changed to the second imaging sensitivity in Step S202a, the determination circuit 102 uses the threshold value A2 in Step S203. When the imaging sensitivity of the imaging device 103 is changed to the first imaging sensitivity in Step S202a, the determination circuit 102 uses a threshold value A2a in Step S203. The first imaging sensitivity is smaller than the second imaging sensitivity. The threshold value A2a is less than the threshold value A2. In other words, the third brightness when the imaging sensitivity of the imaging device 103 is the first imaging sensitivity is darker than the third brightness when the imaging sensitivity of the imaging device 103 is the second imaging sensitivity.

The methods described in the second modified example of the first embodiment may be applied to the wireless endoscope system 10a shown in FIG. 10.

In the second modified example of the first embodiment, when the determination circuit 102 determines that the value indicating the brightness of the image is less than or equal to the threshold value A1 the control circuit 101 changes the imaging sensitivity of the imaging device 103 in accordance with the brightness of the image. Therefore, the control circuit 101 can set imaging sensitivity corresponding to the brightness around the transmission terminal 100 to the imaging device 103. Consequently, the control circuit 101 can control the power consumption of the transmission terminal 100.

Third Modified Example of First Embodiment

A third modified example of the first embodiment of the present invention will be described by using the wireless endoscope system 10 shown in FIG. 1.

Figure 16:
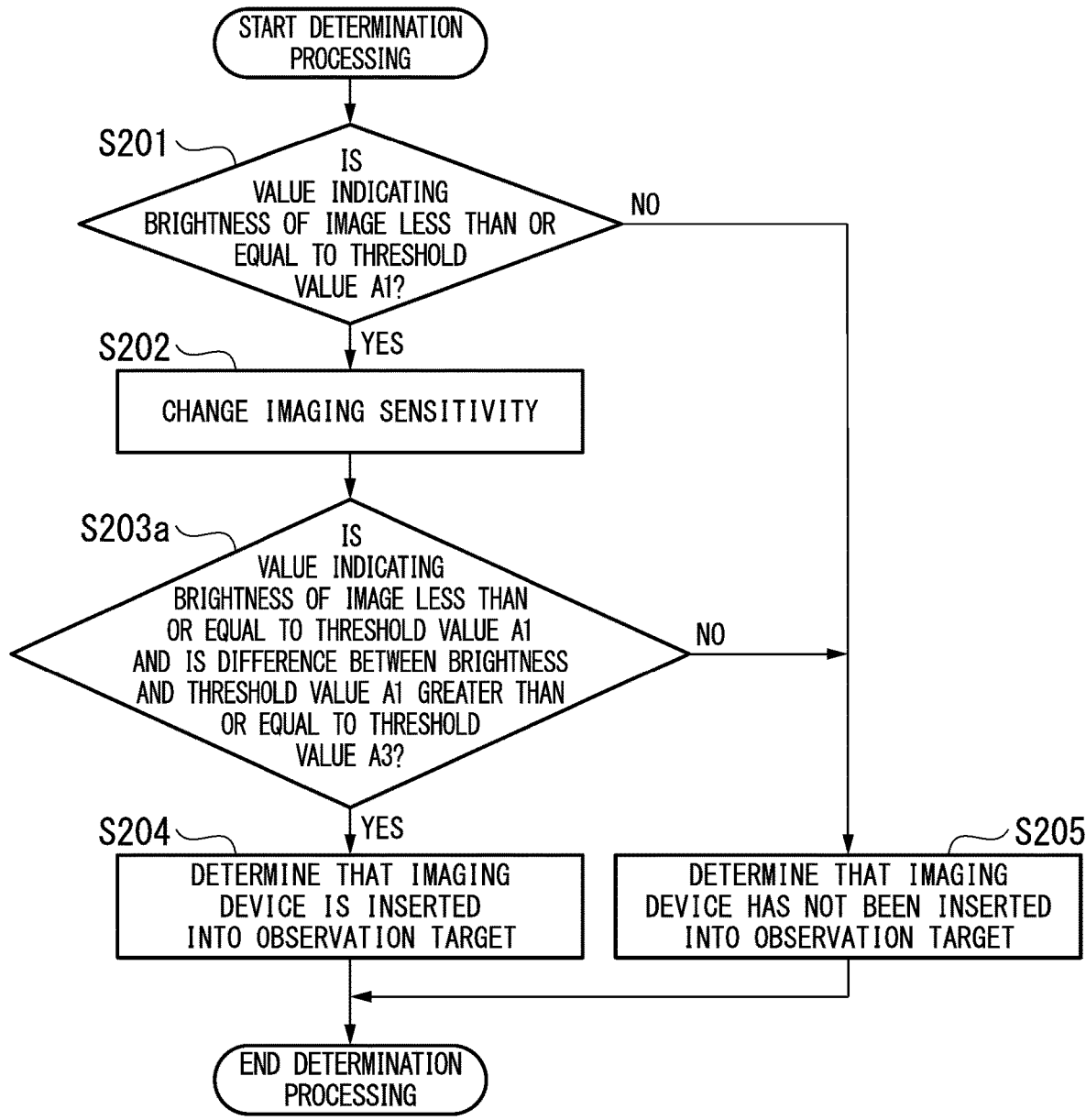
FIG. 16 is a flow chart showing a procedure of an operation of a transmission terminal according to a third modified example of the first embodiment of the present invention.

FIG. 16 shows details of the determination processing in Step S101 shown in FIG. 4. An operation of the transmission terminal 100 in the determination processing will be described with reference to FIG. 16. The same processing as that shown in FIG. 5 will not be described.

After Step S202, the determination circuit 102 detects the brightness of the image output from the imaging device 103. The determination circuit 102 determines whether or not the value indicating the brightness of the image is less than the threshold value A1 and the difference between the value and the threshold value A1 is greater than or equal to a threshold value A3 (Step S203a). The value less than the threshold value A3 by the threshold value A1 indicates the second brightness. The threshold value A3 is experimentally decided. The image generated by the imaging device 103 after Step S102 is executed is used in Step S203a.

When the determination circuit 102 determines that the value indicating the brightness of the image is less than the threshold value A1 and the difference between the value and the threshold value A1 is greater than or equal to the threshold value A3 in Step S203a, Step S204 is executed. When the value indicating the brightness of the image is greater than or equal to the threshold value A1 in Step S203a, Step S205 is executed. When the determination circuit 102 determines that the value indicating the brightness of the image is less than the threshold value A1 and the difference between the value and the threshold value A1 is less than the threshold value A3 in Step S203a, Step S205 is executed.

FIGS. 17 to 20 show the change in the brightness of an image. The horizontal axis of the graph shown in each drawing indicates time, and the vertical axis of the graph shown in each drawing indicates the brightness of an image.

Figure 17:
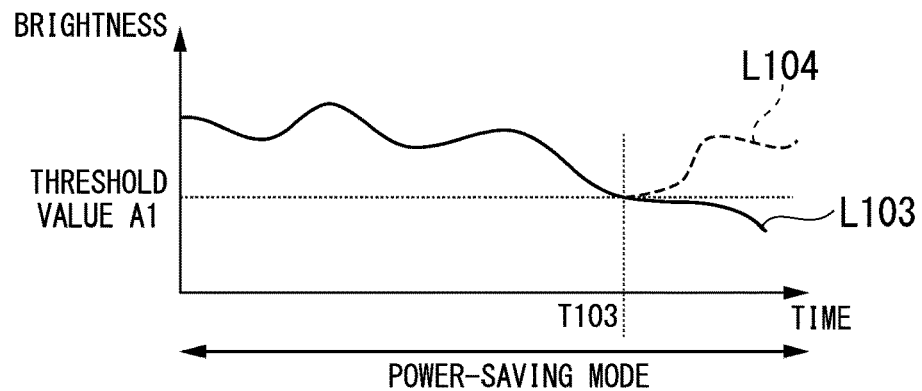
FIG. 17 is a graph showing the change in the brightness of an image in the third modified example of the first embodiment of the present invention.

In FIG. 17, the value indicating the brightness of an image generated before a time point T103 is greater than the threshold value A1. Therefore, the determination circuit 102 determines that the imaging device 103 is not inserted into the observation target. The operation mode of the transmission terminal 100 is maintained in the power-saving mode until the time point T103. The value indicating the brightness of an image generated at the time point T103 is less than or equal to the threshold value A1. Therefore, the control circuit 101 increases the imaging sensitivity of the imaging device 103. In a case in which the imaging device 103 is used in a very dark place, the image becomes dark, as the line L103 shows. In a case in which the imaging device 103 is used in a slightly dark place, the image may become bright due to the increase in the imaging sensitivity, as the line L104 shows. The operation mode of the transmission terminal 100 is maintained in the power-saving mode even after the time point T103.

Figure 18:
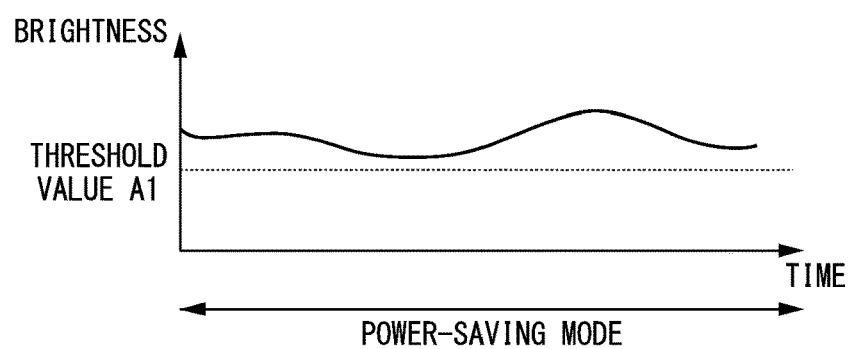
FIG. 18 is a graph showing the change in the brightness of an image in the third modified example of the first embodiment of the present invention.

In FIG. 18, the brightness of an image is always greater than the threshold value A1. Therefore, the determination circuit 102 determines that the imaging device 103 is not inserted into the observation target. The operation mode of the transmission terminal 100 is maintained in the power-saving mode.

Figure 19:
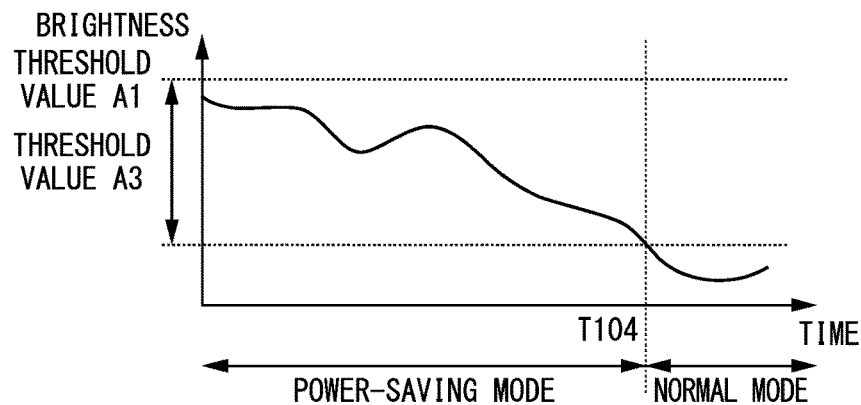
FIG. 19 is a graph showing the change in the brightness of an image in the third modified example of the first embodiment of the present invention.

FIG. 19 shows the change in the brightness of an image generated after the imaging sensitivity of the imaging device 103 increases. The value indicating the brightness of an image generated before a time point T104 is less than the threshold value A1. In addition, the difference between the value and the threshold value A1 is less than the threshold value A3. Therefore, the determination circuit 102 determines that the imaging device 103 is not inserted into the observation target. The operation mode of the transmission terminal 100 is maintained in the power-saving mode until the time point T104. The difference between the value indicating the brightness of an image generated at the time point T104 and the threshold value A1 is greater than or equal to the threshold value A3. Therefore, the determination circuit 102 determines that the imaging device 103 is inserted into the observation target. The control circuit 101 changes the operation mode of the transmission terminal 100 to the normal mode.

Figure 20:
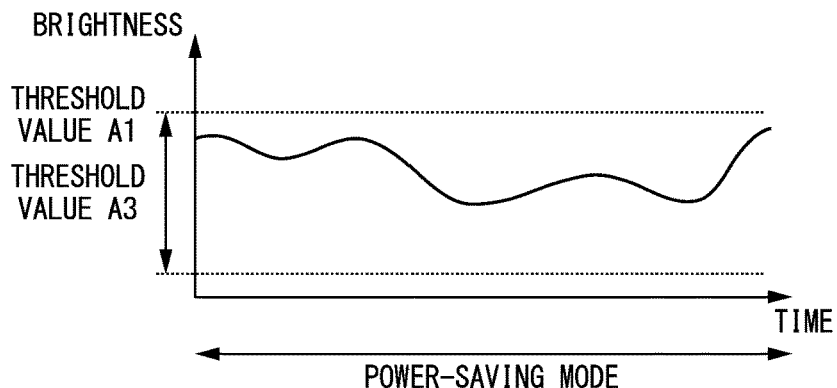
FIG. 20 is a graph showing the change in the brightness of an image in the third modified example of the first embodiment of the present invention.

FIG. 20 shows the change in the brightness of an image generated after the imaging sensitivity of the imaging device 103 increases. The brightness of an image is always less than the threshold value A1. In addition, the difference between the value indicating the brightness of an image and the threshold value A1 is always less than the threshold value A3. Therefore, the determination circuit 102 determines that the imaging device 103 is not inserted into the observation target. The operation mode of the transmission terminal 100 is maintained in the power-saving mode.

The methods described in the third modified example of the first embodiment may be applied to the wireless endoscope system 10a shown in FIG. 10.

In the third modified example of the first embodiment, the determination circuit 102 can determine whether or not the imaging device 103 is inserted into the observation target by using a similar method to that shown in FIG. 5.

Second Embodiment

A second embodiment of the present invention will be described by using the wireless endoscope system 10 shown in FIG. 1. When the determination circuit 102 determines that the brightness of an image is darker than or equal to the third brightness, the control circuit 101 causes the transmission terminal 100 to operate in the normal mode. The third brightness is darker than the first brightness. When the determination circuit 102 determines that the brightness of the image is darker than or equal to the first brightness and is brighter than the third brightness, the control circuit 101 increases the imaging sensitivity of the imaging device 103.

Figure 21:
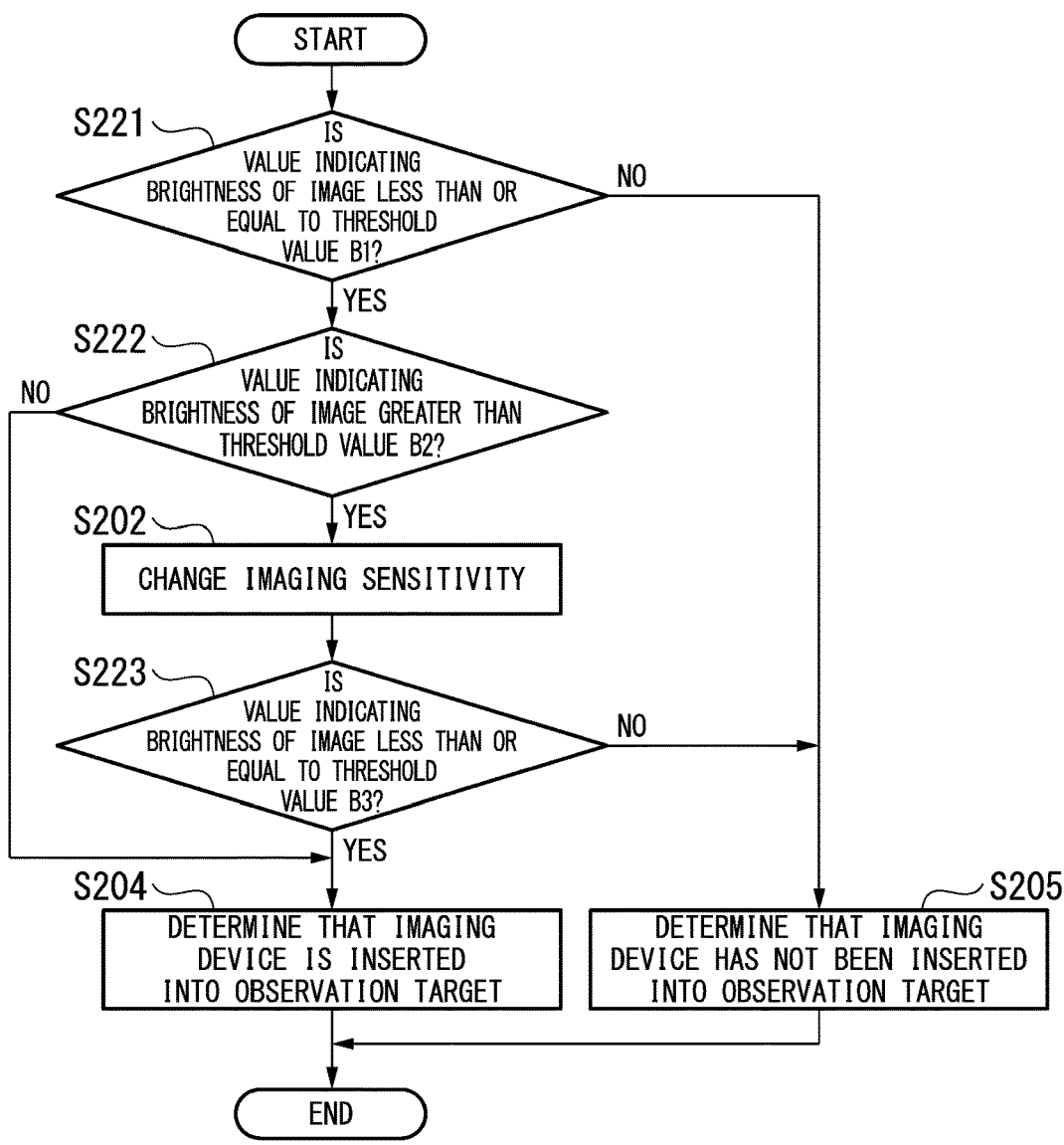
FIG. 21 is a flow chart showing a procedure of an operation of a transmission terminal according to a second embodiment of the present invention.

FIG. 21 shows details of the determination processing in Step S101 shown in FIG. 4. An operation of the transmission terminal 100 in the determination processing will be described with reference to FIG. 21. The same processing as that shown in FIG. 5 will not be described.

The determination circuit 102 detects the brightness of the image output from the imaging device 103 and determines whether or not the value indicating the brightness is less than or equal to a threshold value B1 (Step S221). The threshold value B1 indicates the first brightness. For example, the threshold value B1 is experimentally decided. The threshold value B1 may be the same as the threshold value A1 shown in FIG. 5.

When the determination circuit 102 determines that the value indicating the brightness of the image is greater than the threshold value B1 in Step S221, Step S202 is executed. When the determination circuit 102 determines that the value indicating the brightness of the image is less than or equal to the threshold value B1 in Step S221, the determination circuit 102 determines whether or not the value indicating the brightness of the image is greater than a threshold value B2 (Step S222). The threshold value B2 indicates the third brightness. For example, the threshold value B2 is less than the threshold value B1. For example, the threshold value B2 is experimentally decided. The image used for the determination in Step S221 is used in Step S222.

When the determination circuit 102 determines that the value indicating the brightness of the image is greater than the threshold value B2 in Step S222, Step S202 is executed. When the determination circuit 102 determines that the value indicating the brightness of the image is less than or equal to the threshold value B2 in Step S222, Step S204 is executed.

After Step S202, the determination circuit 102 detects the brightness of the image output from the imaging device 103 and determines whether or not the value indicating the brightness is less than or equal to a threshold value B3 (Step S223). The threshold value B3 indicates the second brightness. The threshold value B3 is less than the threshold value B1. For example, the threshold value B3 is experimentally decided. The threshold value B3 may be the same as the threshold value A2 shown in FIG. 5. The image generated by the imaging device 103 after Step S202 is executed is used in Step S223.

When the determination circuit 102 determines that the value indicating the brightness of the image is less than or equal to the threshold value B3 in Step S223, Step S204 is executed. When the determination circuit 102 determines that the value indicating the brightness of the image is greater than the threshold value B3 in Step S223, Step S205 is executed.

Before the imaging sensitivity of the imaging device 103 increases, the determination circuit 102 detects the environment in which the imaging device 103 is used by determining the brightness of the image in Step S222. When it is possible to determine that the image is sufficiently dark in Step S222, the determination circuit 102 determines that the imaging device 103 is inserted into the observation target in Step S204. When the image is determined to be not sufficiently dark in Step S222, there is a possibility that the imaging device 103 is not inserted into the observation target and is used in a dark place outside the observation target. In order to determine whether the imaging device 103 is inserted into the observation target or is used in a dark place outside the observation target, the control circuit 101 increases the imaging sensitivity of the imaging device 103 in Step S202. After the imaging sensitivity of the imaging device 103 increases, Step S223 is executed in order to determine whether or not the imaging device 103 is inserted into the observation target.

There is a possibility that the brightness of an image changes in accordance with the change in the imaging sensitivity of the imaging device 103 even when the brightness around the transmission terminal 100 is fixed. After the imaging sensitivity of the imaging device 103 increases, the image tends to become brighter. Therefore, there is a possibility that the determination result of Step S222 and the determination result of Step S223 are different from each other in a case in which the imaging device 103 is inserted into the observation target. In light of this, the threshold value B2 in Step S222 may be less than the threshold value B3 in Step S223. In other words, the third brightness may be darker than the second brightness.

FIGS. 22 to 25 show the change in the brightness of an image. The horizontal axis of the graph shown in each drawing indicates time, and the vertical axis of the graph shown in each drawing indicates the brightness of an image.

Figure 22:
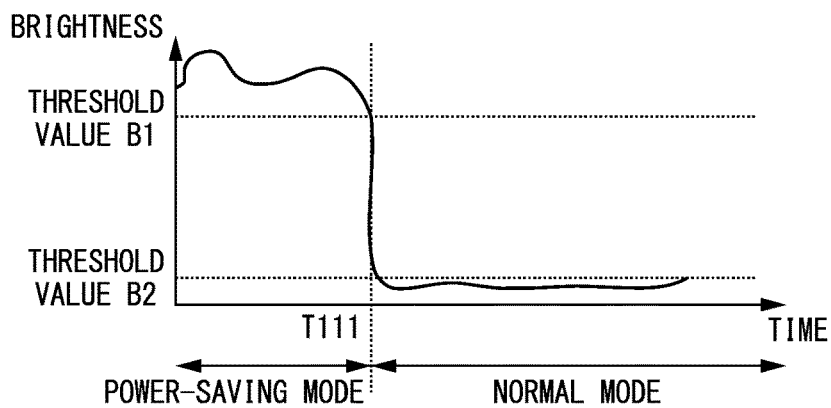
FIG. 22 is a graph showing the change in the brightness of an image in the second embodiment of the present invention.

In FIG. 22, the value indicating the brightness of an image generated before a time point T111 is greater than the threshold value B1. Therefore, the determination circuit 102 determines that the imaging device 103 is not inserted into the observation target. The operation mode of the transmission terminal 100 is maintained in the power-saving mode until the time point T111. The value indicating the brightness of an image generated at the time point T111 is less than or equal to the threshold value B1 and is less than the threshold value B2. Therefore, the determination circuit 102 determines that the imaging device 103 is inserted into the observation target. The control circuit 101 changes the operation mode of the transmission terminal 100 to the normal mode.

Figure 23:
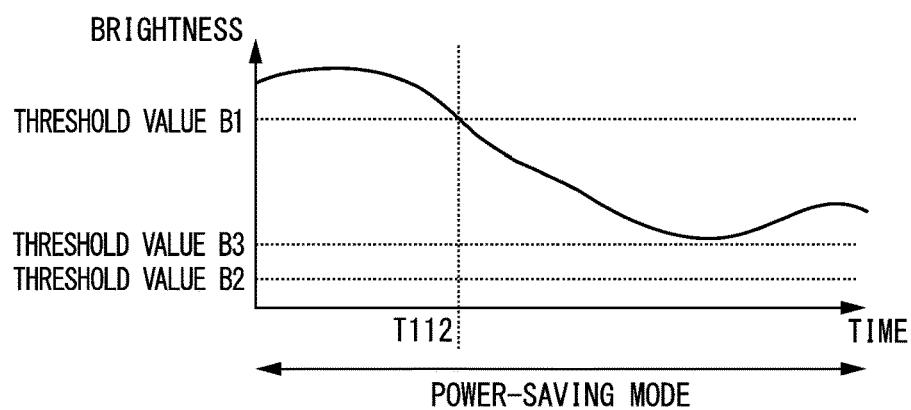
FIG. 23 is a graph showing the change in the brightness of an image in the second embodiment of the present invention.

In FIG. 23, the value indicating the brightness of an image generated before a time point T112 is greater than the threshold value B1. Therefore, the determination circuit 102 determines that the imaging device 103 is not inserted into the observation target. The operation mode of the transmission terminal 100 is maintained in the power-saving mode until the time point T112. The value indicating the brightness of an image generated at the time point T112 is less than or equal to the threshold value B1 and is greater than the threshold value B2. Therefore, the control circuit 101 increases the imaging sensitivity of the imaging device 103. The value indicating the brightness of an image generated after the time point T112 is less than or equal to the threshold value B1, but is greater than any of the threshold value B2 and the threshold value B3. Therefore, the determination circuit 102 determines that the imaging device 103 is not inserted into the observation target. The operation mode of the transmission terminal 100 is maintained in the power-saving mode even after the time point T112.

Figure 24:
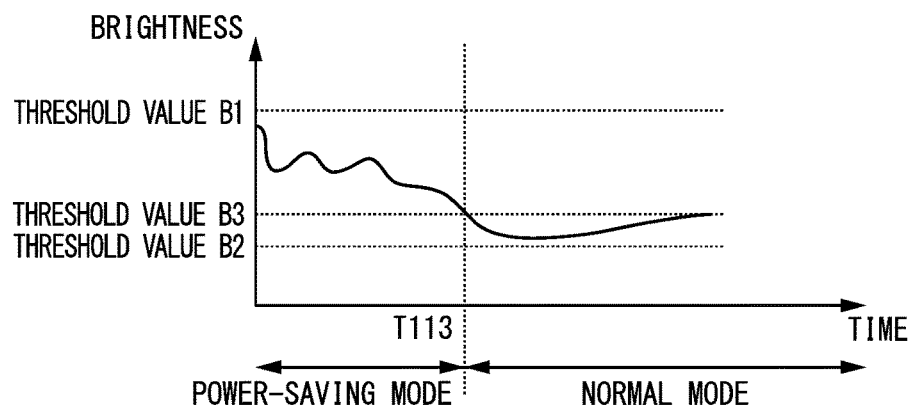
FIG. 24 is a graph showing the change in the brightness of an image in the second embodiment of the present invention.

FIG. 24 shows the change in the brightness of an image generated after the imaging sensitivity of the imaging device 103 increases. The value indicating the brightness of an image generated before a time point T113 is less than the threshold value B1 and is greater than the threshold value B3. Therefore, the determination circuit 102 determines that the imaging device 103 is not inserted into the observation target. The operation mode of the transmission terminal 100 is maintained in the power-saving mode until the time point T113. The value indicating the brightness of an image generated at the time point T113 is less than or equal to the threshold value B3. Therefore, the determination circuit 102 determines that the imaging device 103 is inserted into the observation target. The control circuit 101 changes the operation mode of the transmission terminal 100 to the normal mode.

Figure 25:
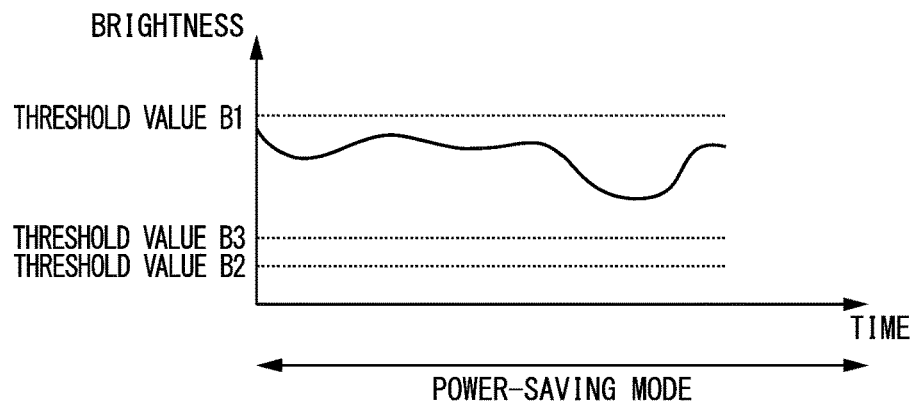
FIG. 25 is a graph showing the change in the brightness of an image in the second embodiment of the present invention.

FIG. 25 shows the change in the brightness of an image generated after the imaging sensitivity of the imaging device 103 increases. The brightness of an image is always less than the threshold value B1. In addition, the brightness of an image is always greater than the threshold value B2 and is greater than the threshold value B3. Therefore, the determination circuit 102 determines that the imaging device 103 is not inserted into the observation target. The operation mode of the transmission terminal 100 is maintained in the power-saving mode.

The methods described in the second embodiment may be applied to the wireless endoscope system 10a shown in FIG. 10.

In the second embodiment, the power consumption of the transmission terminal 100 is suppressed. In addition, the transmission terminal 100 can correctly determine whether or not the imaging device 103 is inserted into the observation target.

Before the imaging sensitivity of the imaging device 103 increases, the environment in which the imaging device 103 is used is detected in Step S222. When the imaging device 103 has already been inserted into the observation target, the transmission terminal 100 can quickly shift the operation mode to the normal mode.

Third Embodiment

A third embodiment of the present invention will be described by using the wireless endoscope system 10 shown in FIG. 1. After the transmission terminal 100 starts to operate in the normal mode, the control circuit 101 causes the transmission terminal 100 to operate in the power-saving mode. After the operation mode of the transmission terminal 100 is changed from the normal mode to the power-saving mode, the control circuit 101 causes the transmission terminal 100 to operate in the normal mode when the determination circuit 102 determines that the brightness of an image is darker than or equal to the third brightness. The third brightness is darker than the first brightness. After the operation mode of the transmission terminal 100 is changed from the normal mode to the power-saving mode, the control circuit 101 increases the imaging sensitivity of the imaging device 103 when the determination circuit 102 determines that the brightness of the image is brighter than the third brightness and is darker than or equal to the first brightness.

Figure 26:
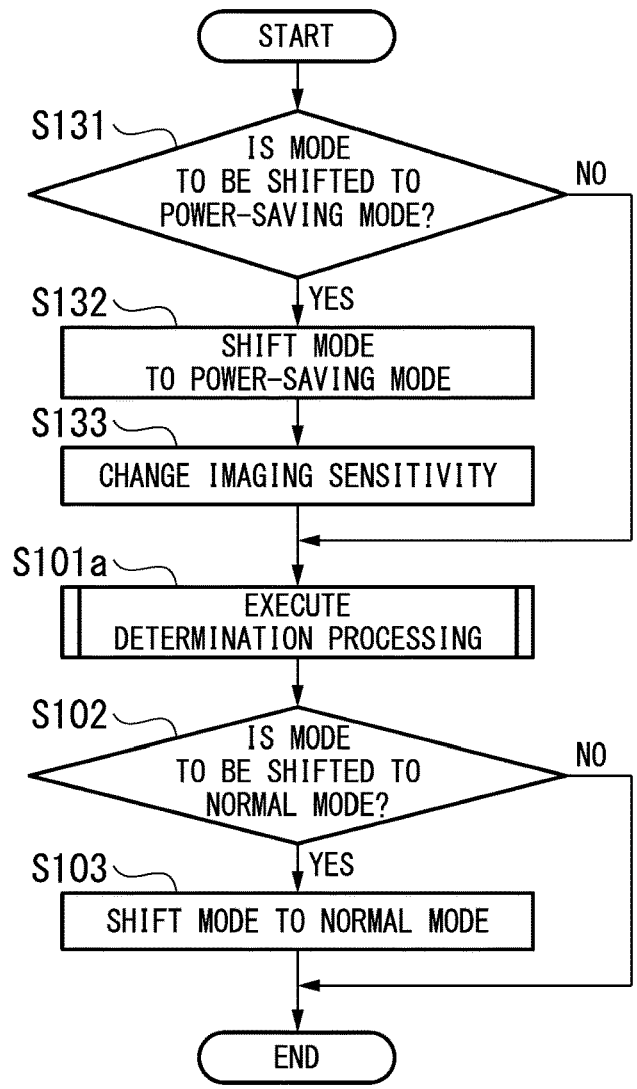
FIG. 26 is a flow chart showing a procedure of an operation of a transmission terminal according to a third embodiment of the present invention.

FIG. 26 shows a procedure of an operation of the transmission terminal 100. An operation of the transmission terminal 100 will be described with reference to FIG. 26. The same processing as that shown in FIG. 4 will not be described.

The control circuit 101 determines whether or not to shift the operation mode to the power-saving mode (Step S131). The wireless endoscope system 10 can shift the operation mode to the power-saving mode by using various methods. When observation in the observation target is completed, the imaging device 103 is pulled out of the observation target. The brightness of an image is different in accordance with the observation target. Even when the light source 104 is turned on, an image becomes darker than that at the time of observation if the imaging device 103 goes out of the observation target. Therefore, the control circuit 101 determines to shift the operation mode to the power-saving mode. The control circuit 101 may execute the determination in Step S131 by using a method other than that using an image. When the transmission terminal 100 is operating in the power-saving mode, the control circuit 101 determines not to shift the operation mode to the power-saving mode.

When the control circuit 101 determines not to shift the operation mode to the power-saving mode in Step S131, Step S101a is executed. Step S101 shown in FIG. 4 is changed to Step S101a. When the control circuit 101 determines to shift the operation mode to the power-saving mode in Step S131, the control circuit 101 causes the transmission terminal 100 to operate in the power-saving mode (Step S132).

The control circuit 101 makes power consumption of the control target less than that in the normal mode in Step S132. The control circuit 101 changes the mode of the transmission terminal 100 from the normal mode to the power-saving mode in Step S132. Mode information indicating the power-saving mode is stored on the RAM 108.

After Step S132, the control circuit 101 changes the imaging sensitivity of the imaging device 103 (Step S133). For example, the control circuit 101 reduces the imaging sensitivity by shortening the exposure time of the imaging device 103 in Step S133. The exposure time after Step S133 is executed is shorter than the exposure time before Step S133 is executed. Alternatively, the control circuit 101 reduces the imaging sensitivity by reducing the gain of the imaging device 103. The gain after Step S133 is executed is less than the gain before Step S133 is executed. After Step S133, Step S101a is executed.

Figure 27:
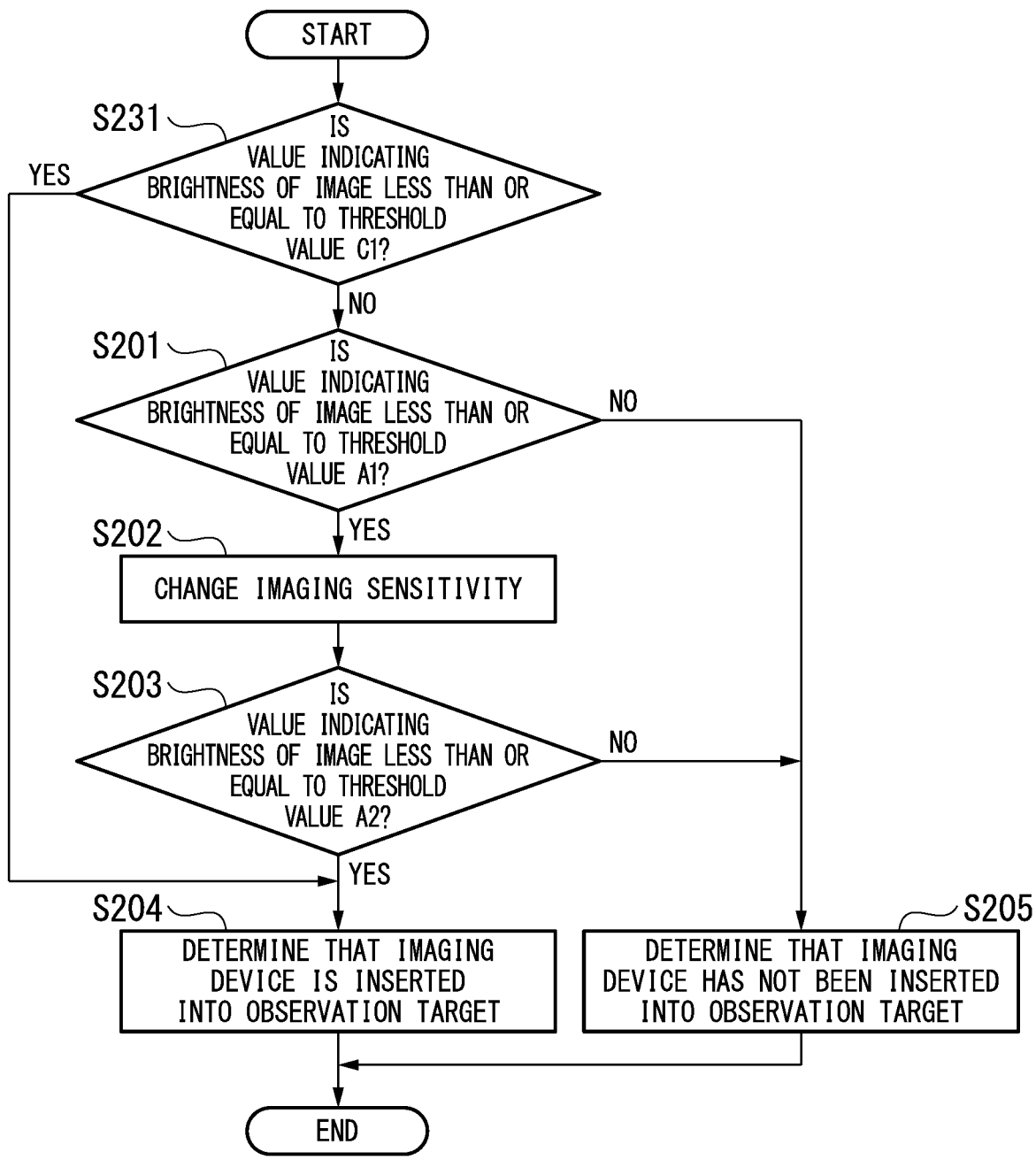
FIG. 27 is a flow chart showing a procedure of an operation of the transmission terminal according to the third embodiment of the present invention.

FIG. 27 shows details of the determination processing in Step S101a shown in FIG. 26. An operation of the transmission terminal 100 in the determination processing will be described with reference to FIG. 27. The same processing as that shown in FIG. 5 will not be described.

The determination circuit 102 detects the brightness of the image output from the imaging device 103 and determines whether or not the value indicating the brightness is less than or equal to a threshold value C1 (Step S231). The threshold value C1 is less than the threshold value A1. The threshold value C1 indicates the third brightness. For example, the threshold value C1 is experimentally decided.

When the determination circuit 102 determines that the value indicating the brightness of the image is greater than the threshold value C1 in Step S231, Step S201 is executed. When the determination circuit 102 determines that the value indicating the brightness of the image is less than or equal to the threshold value C1 in Step S231, Step S204 is executed.

Immediately after the transmission terminal 100 shifts the operation mode to the power-saving mode, the determination circuit 102 detects the environment in which the imaging device 103 is used by determining the brightness of the image in Step S231. When it is possible to determine that the image is sufficiently dark in Step S231, the determination circuit 102 determines that the imaging device 103 is inserted into the observation target in Step S204. When the image is determined to be not sufficiently dark in Step S231, there is a possibility that the imaging device 103 is not inserted into the observation target and is used in a dark place. In order to determine whether the imaging device 103 is inserted into the observation target or is used in a dark place, the control circuit 101 increases the imaging sensitivity of the imaging device 103 in Step S202. After the imaging sensitivity of the imaging device 103 increases, Step S204 is executed in order to determine whether or not the imaging device 103 is inserted into the observation target.

Step S231 may be executed only after Step S132 and Step S133 are executed. When Step S132 and Step S133 have not been executed, the transmission terminal 100 is operating in the normal mode. In such a case, Step S201 may be executed without Step S231 being executed in the determination processing.

There is a possibility that the brightness of an image changes in accordance with the change in the imaging sensitivity of the imaging device 103 even when the brightness around the transmission terminal 100 is fixed. After the imaging sensitivity of the imaging device 103 increases, the image tends to become brighter. Therefore, there is a possibility that the determination result of Step S231 and the determination result of Step S203 are different from each other in a case in which the imaging device 103 is inserted into the observation target. In light of this, the threshold value C1 in Step S231 may be less than the threshold value A2 in Step S203. In other words, the third brightness may be darker than the second brightness.

Figure 28:
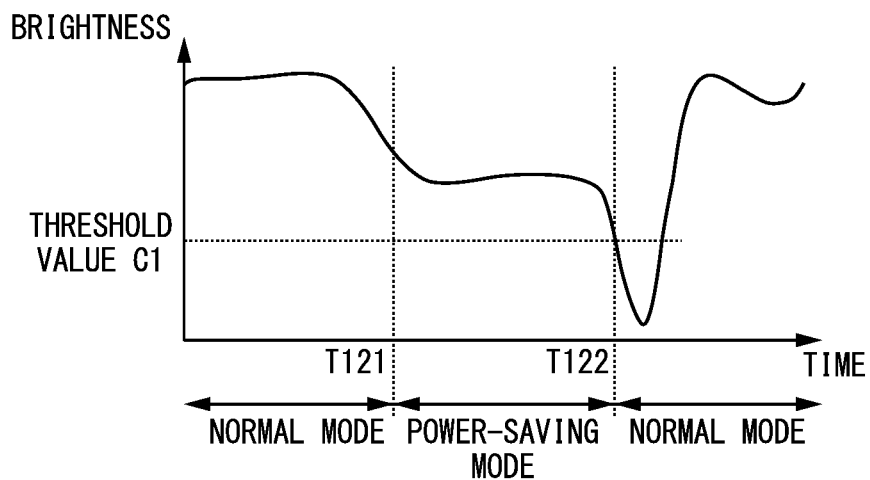
FIG. 28 is a graph showing the change in the brightness of an image in the third embodiment of the present invention.
Figure 29:
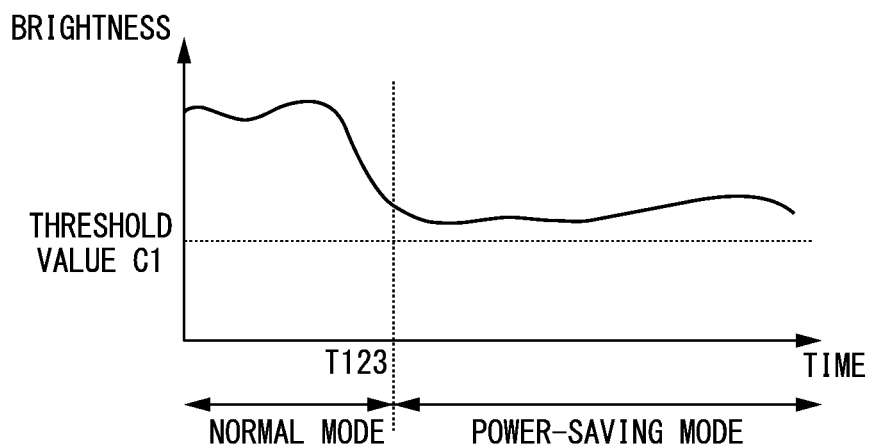
FIG. 29 is a graph showing the change in the brightness of an image in the third embodiment of the present invention.

FIG. 28 and FIG. 29 show the change in the brightness of an image. The horizontal axis of the graph shown in each drawing indicates time, and the vertical axis of the graph shown in each drawing indicates the brightness of an image.

In FIG. 28, the operation mode of the transmission terminal 100 is changed from the normal mode to the power-saving mode at a time point T121. The value indicating the brightness of an image generated after the time point T121 and before a time point T122 is greater than the threshold value C1. Therefore, the determination circuit 102 determines that the imaging device 103 is not inserted into the observation target. The operation mode of the transmission terminal 100 is maintained in the power-saving mode until the time point T122. The value indicating the brightness of an image generated at the time point T122 is less than or equal to the threshold value C1. Therefore, the determination circuit 102 determines that the imaging device 103 is inserted into the observation target. The control circuit 101 changes the operation mode of the transmission terminal 100 to the normal mode.

In FIG. 29, the operation mode of the transmission terminal 100 is changed from the normal mode to the power-saving mode at a time point T123. After the time point T123, the value indicating the brightness of an image is greater than the threshold value C1. Therefore, the determination circuit 102 determines that the imaging device 103 is not inserted into the observation target. The operation mode of the transmission terminal 100 is maintained in the power-saving mode.

The methods described in the third embodiment may be applied to the wireless endoscope system 10a shown in FIG. 10.

In the third embodiment, the power consumption of the transmission terminal 100 is suppressed. In addition, the transmission terminal 100 can correctly determine whether or not the imaging device 103 is inserted into the observation target.

Immediately after the transmission terminal 100 shifts the operation mode to the power-saving mode, the environment in which the imaging device 103 is used is detected in Step S222. When the imaging device 103 is inserted into the observation target again, the transmission terminal 100 can quickly shift the operation mode to the normal mode.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging apparatus configured to operate in any one of a first operation mode and a second operation mode, an amount of power consumption in the second operation mode being less than an amount of power consumption in the first operation mode,
the imaging apparatus comprising:
an imaging device configured to generate an image; and
a processor is configured to:
determine brightness of the image when the imaging apparatus is operating in the second operation mode;
increase imaging sensitivity of the imaging device when the processor determines that the brightness is darker than or equal to a first brightness; and
cause the imaging apparatus to operate in the first operation mode when the processor determines that the brightness is darker than or equal to a second brightness darker than the first brightness after the processor increases the imaging sensitivity.

2. The imaging apparatus according to claim 1, wherein the processor is configured to increase the imaging sensitivity by lengthening an exposure time of the imaging device.

3. The imaging apparatus according to claim 1, wherein the processor is configured to increase the imaging sensitivity by increasing gain of the imaging device.

4. The imaging apparatus according to claim 1, wherein the processor is configured to:
change the imaging sensitivity to a first imaging sensitivity by increasing the imaging sensitivity when the processor determines that the brightness is darker than or equal to the first brightness and is brighter than a third brightness,
wherein the third brightness is brighter than the second brightness and is darker than the first brightness; and
change the imaging sensitivity to a second imaging sensitivity by increasing the imaging sensitivity when the processor determines that the brightness is darker than or equal to the third brightness,
wherein the second imaging sensitivity is higher than the first imaging sensitivity.

5. The imaging apparatus according to claim 4, wherein the third brightness when the imaging sensitivity is the first imaging sensitivity is darker than the third brightness when the imaging sensitivity is the second imaging sensitivity.

6. The imaging apparatus according to claim 1, wherein the processor is configured to determine that the imaging device is inserted into an observation target when the brightness is darker than or equal to the second brightness.

7. The imaging apparatus according to claim 1, wherein the processor is configured to:
cause the imaging apparatus to operate in the first operation mode when the processor determines that the brightness is darker than or equal to a third brightness,
wherein the third brightness is darker than the first brightness; and
increase the imaging sensitivity when the processor determines that the brightness is darker than or equal to the first brightness and is brighter than the third brightness.

8. The imaging apparatus according to claim 7, wherein the third brightness is darker than the second brightness.

9. The imaging apparatus according to claim 1, wherein the processor is configured to:
cause the imaging apparatus to operate in the second operation mode after the imaging apparatus starts to operate in the first operation mode;
cause the imaging apparatus to operate in the first operation mode when the processor determines that the brightness is darker than or equal to a third brightness after an operation mode of the imaging apparatus is changed from the first operation mode to the second operation mode,
wherein the third brightness is darker than the first brightness; and
increase the imaging sensitivity when the processor determines that the brightness is brighter than the third brightness and is darker than or equal to the first brightness after the operation mode of the imaging apparatus is changed from the first operation mode to the second operation mode.

10. The imaging apparatus according to claim 9, wherein the third brightness is darker than the second brightness.

11. A non-transitory computer-readable recording medium saving a program for causing a processor of an imaging apparatus configured to operate in any one of a first operation mode and a second operation mode wherein an amount of power consumption in the second operation mode is less than an amount of power consumption in the first operation mode, the processor is configured to execute:
a first step in which the processor determines brightness of an image generated by an imaging device when the imaging apparatus is operating in the second operation mode;
a second step in which the processor increases imaging sensitivity of the imaging device when the processor determines that the brightness is darker than or equal to a first brightness; and
a third step in which the processor causes the imaging apparatus to operate in the first operation mode when the processor determines that the brightness is darker than or equal to a second brightness darker than the first brightness after the processor increases the imaging sensitivity.

* * * * *